US007816506B2

(12) United States Patent
Mirkov et al.

(10) Patent No.: US 7,816,506 B2
(45) Date of Patent: Oct. 19, 2010

(54) METHODS AND CONSTRUCTS FOR PRODUCING TRANSGENIC PLANTS AND METHODS OF RECOVERING EXPRESSED PROTEINS

(75) Inventors: T. Erik Mirkov, Harlingen, TX (US); Andrew Paterson, Arnoldsville, GA (US); Meizhu Yang, Johnston, IA (US)

(73) Assignee: The Texas A & M University System, College Station, TX (US)

( * ) Notice: Subject to any disclaimer, the term of this patent is extended or adjusted under 35 U.S.C. 154(b) by 275 days.

(21) Appl. No.: 12/188,069

(22) Filed: Aug. 7, 2008

(65) Prior Publication Data
US 2010/0031396 A1 Feb. 4, 2010

Related U.S. Application Data

(63) Continuation of application No. 11/558,247, filed on Nov. 9, 2006, which is a continuation of application No. 10/257,157, filed as application No. PCT/AU01/00418 on Apr. 11, 2001, now Pat. No. 7,141,427.

(60) Provisional application No. 60/196,085, filed on Apr. 11, 2000.

(51) Int. Cl.
*C07H 21/04* (2006.01)
*C12N 15/82* (2006.01)
(52) U.S. Cl. ..................... 536/23.4; 800/278
(58) Field of Classification Search ........................ None
See application file for complete search history.

(56) References Cited

U.S. PATENT DOCUMENTS 5,097,025 A    3/1992   Benfey et al. .................. 536/27
6,479,636 B1   11/2002  Mirkov et al. ............... 530/379

FOREIGN PATENT DOCUMENTS

WO           91/13991           9/1991

OTHER PUBLICATIONS

Abencibia, et al. "Production of Transgenic Sugarcane (*Saccharum officinarum* L.) Plants by Intact Cell Electroporation" Plant Cell Reports, vol. 14, pp. 305-309, 1995.
Arencibia, et al. "An Efficient Protocol for Sugarcane (*Saccharum* spp. L.) Transformation Mediated by *Agrobacterium tumefaciens*" Transgenic Research., vol. 7, pp. 213-222, 1998.
Arencibia, et al. "Transgenic Sugarcane Plants Resistant to Stem Borer Attack" Molecular Breeding, vol. 3, pp. 247-255, 1997.
Arumuganathan et al. "Nuclear DNA Content of Some Important Plant Species" Plant Molecular Biology Reporter, vol. 9, pp. 208-219, 1991.
Axelos, et al. "The Gene Family Encoding the *Arabidopsis thaliana* Translation Elongation Factor EF-1α: Molecule Cloning, Characterization and Expression" Molecular & General Genetics, vol. 219, pp. 106-112, 1989.

Benfey, et al. "Combinatorial and Synergistic Properties of CaMV 35S Enhancer Subdomains" EMBO J, vol. 9, pp, 1685-1696, 1990.
Berberich, et al. "Molecular Cloning, Characterization and Expression of an Elongation Factor 1α Gene in Maize" Plant Molecular Biology, vol. 29, pp. 611-615, 1995.
Bevan "A Chimeric Antibiotic Resistance Gene as a Selectable Marker for Plant Cell Transformation" Nature, vol. 304, pp. 184-187, 1983.
Bevan, et al. "Analysis of 1.9 Mb of Contiguous Sequence From Chromosome 4 of *Arabidopsis thaliana*" Nature, vol. 391, pp. 485-488, 1998.
Bower, et al. "High-Efficiency Microprojectile-Midiated Cotransformation of Sugarcane, Using Visible or Selectable Markers" Molecular Breeding, vol. 2, pp. 239-249, 1996.
Bower, et al. "Transgenic Sugarcane Plants via Microprojectile Bombardment" Plant J, vol. 2(3), pp. 409-416, 1992.
Callis, et al. "Introns Increase Gene Expression in Cultured Maize Cells" Genes & Development, vol. 1, pp. 1183-1200, 1987.
Callis, et al. "Ubiquitin Extension Proteins of *Arabidopsis thaliana*. Structure, Localization, and Expression of their Promoters in Transgenic Tobacco" J Biological Chemistry, vol. 265, pp. 12486-12493, 1990.
Chen, et al. "Efficient Transcription From the Rice Tungro Bacillform Virus Promoter Requires Elements Downstream of the Transcription Start Site" J Virology, vol. 70, pp. 8411-8421, 1996.
Christensen, et al. "Ubiquitin Promoter-Based Vectors for High-Level Expression of Selectable and/or Screenable Marker Genes in Monocotyledonous Plants" Transgenic Research, vol. 5, pp. 213-218, 1996.
Christensen, et al. "Maize Polyubiquitin Genes: Structure, Thermal Perturbation of Expression and Transcript Splicing, and Promoter Activity Following Transfer to Protoplasts by Electroporation" Plant Molecular Biology, vol. 18, pp. 675-689, 1992.
Curie, et al. "Modular Organization and Development Activity of an *Arabidopsis thaliana* EF-1α Gene Promoter" Molecular & General Genetics, vol. 238, pp. 428-436, 1993.
Curie, et al. "Cis and Trans-Acting Elements Involved in the Activation of *Arabidopsis thaliana* A1 Gene Encoding the Translation Elongation Factor EF-1α" Nucleic Acids Research vol. 19, pp. 1305-1310, 1991.
D'Hont, et al. "Characterisation of the Double Genome Structure of Modern Sugarcane Cultivars (*Saccharum* spp.) by Molecular Cytogenetics" Molecular & General Genetics., vol. 250, pp. 405-413, 1996.
Elomaa, et al. "Transgene Inactivation in *Petunia hybrida* is Influenced by the Properties of the Foreign Gene" Mol.Gen. Genet, vol. 248, pp. 649-656, 1995.
Enriquez, et al. "Herbiciede-Resistant Sugarcane (*Saccharum officinarum* L.) Plants by *Agrobacterium*-Mediated Transformation" Planta, vol. 206, pp. 20-27, 1998.

(Continued)

*Primary Examiner*—Anand U Desai
(74) *Attorney, Agent, or Firm*—King & Spalding L.L.P.

(57) ABSTRACT

This disclosure relates to a regulatory element useful for genetically engineering sugarcane or other monocots, to the transformation of the monocots with the regulatory element so that they produce a desired product, and to the regeneration of the monocots transformed with the regulatory element. In particular the present disclosure provides a nucleic acid encoding a promoter of a Sugarcane Elongation Factor (SEF), for example, as shown in SEQ ID NO: 5.

21 Claims, 17 Drawing Sheets

OTHER PUBLICATIONS

"FAO Statistics", Food and Agriculture Organization, FAO production Yearbook, vol. 40, FAO Statistics Series No. 76, Food and Agricultural Organization, Rome, 1986.

Flavell "Inactivation of Gene Expression in Plants as a Consequence of Specific Sequence Duplication" Proc. National Academy of Sci USA, vol. 91, pp. 3490-3496, 1994.

Fraley, et al. "Expression of Bacterial Genes in Plant Cells" Proc Natl. Acad. Sci. USA, vol. 80, pp. 4803-4807, 1983.

Gallie, et al. "A Translational Enhancer Derived From Tobacco Mosaic Virus is Functionally Equivalent to a Shine-Dalgarno Sequence" Proc. National Academy of Science USA, vol. 86, pp. 129-132, 1989.

Gallie, et al. "The 5'-Leader Sequence of Tobacco Mosaic Virus RNA Enhances the Expression of Foreign Gene Transcripts in Vitro and in Vivo" Nucleic Acids Res, vol. 15, pp. 3257-3273, 1987.

Gallie, et al. "Identification of the Motifs Within the Tobacco Mosaic Virus 5'-Leader Responsible for Enhancing Translation" Nucleic Acids Res, vol. 20, pp. 4631-4638, 1992.

Gallo-Meagher, et al. "Effects of Tissue Type and Promoter Strength on Transient GIS Expression in Sugarcane Following Particle Bombardment" Plant Cell Rep., vol. 12, pp. 666-670, 1993.

Gallo-Meagher, et al. "Herbicide Resistant Transgenic Sugarcane Plants Containing the Bar Gene" Crop Science, vol. 36, pp. 1367-1374, 1996.

Gambley, et al, "Microprojectile Transformation of Sugarcane Meristems and Regeneration of Shoots Expression Beta-Glucuronidase" Plant Cell Rep, vol. 12, pp, 343-346, 1993.

Grant "Dissecting the Mechanisms of Posttranscriptional Gene Silencing: Divide and Conquer" Cell, vol. 96, p. 303, 1999.

Grivett, et al. "RFLP Mapping in Cultivated Sugarcane (*Saccharum* spp.) Genome Organization in a Highly Polyploid and Aneuploid Interspecific Hybrid" Genetics, vol. 142, pp. 987-1000, 1996.

Hamilton, et al. "A Monocot Pollen-Specific Promoter Contains Separable Pollen-Specific and Quantitative Elements" Plant Mol. Biol., vol. 38, pp. 663-669, 1998.

Herrera, et al. "Chimeric Genes as Dominant Selectable Markers in Plant Cells" EMBO vol. 2, pp. 987-995, 1983.

Holtorf, et al. "Comparison of Different Constitutive and Inducible Promoters for the Overexpression of Transgenes in *Arabidopsis thaliana*" Plant Mol. Biol., vol. 29, pp. 637-646, 1995.

Honeycutt, et al. "A Rapid DNA Extraction Method for Sugarcane and Its Relatives" Plant Mol. Biol. Rep, vol. 10, pp. 66-72, 1992.

Jobling, et al. "Enhanced Translation of Chimeric Meswengr RNAs Containing a Plant Viral Untranslated Leader Sequence" Nature, vol. 325, pp. 622-625, 1987.

John, et al. "Characterization of mRNA for a Proline-Rich Protein of Cotton Fiber" Plant Physiol, vol. 108, pp. 669-676, 1995.

Kay, et al. "Duplication of CaMV 35S Promoter Sequences Creates a Stron Enhancer for Plant Genes" Science, vol. 236, pp. 1299-1302, 1987.

Koncz, et al. "The Opine Synthase Genes Carried by Ti Plasmids Contain All Signals Necessary for Expression in Plants" EMBO J, vol. 2, pp. 1597-1603, 1983.

Last, et al. "pEmu: An Improved Promoter for Gene Expression in Cereal Cells" Theor. App. Genet., vol. 81, pp. 581-588, 1991.

Liu, et al. "Mapping of Branchpoint Nucleotides in Mutant Pre-mRNAs Expressed in Plant Cells" Plant Journal, vol. 9, pp. 381-389, 1996.

Luehrsen, et al. "Addition of A- and U-Rich Sequence Increases the Splicing Efficiency of a Deleted Form of a Mize Intron" Plant Mol. Biol., vol. 24, pp. 449-463, 1994.

Luehrsen, et al. "Intron Enhancement of Gene Expression and the Splicing Efficiency of Introns in Maize Cells" Mol. Gen Genet., vol. 225, pp. 81-93, 1991.

Mass, et al. "The Combination of a Novel Stimulatory Element in the First Exon of the Maize Shrunken-1 Gene with the Following Intron 1 Enhances Reporter Gene Expression up to 1000-Fold" Plant Mol., Biol, vol. 16, pp. 199-207, 1991.

Maiti, et al. "Promoter/Leader Delection Analysis and Plant Expression Vectors with the Figwort Mosaic Virus (FMV) Full Length Transcript (FLT) Promoter Containing Single or Double Enhancer Domains" Transgenic Res, vol. 6, pp. 143-156, 1997.

Matzke, et al. "Position Effects and Epigenetic Silencing of Plant Transgenes" Curr. Opin. Plant Biol., vol. 1, pp. 142-148, 1998.

Matzke, et al, "Gene Silencing in Plants: Relevance for Genome Evolution and the Acquisition of Genomic Methylation Patters" Novartis Found Symp., vol. 214, pp. 168-186, 1998.

McElroy, et al. "Isolation of an Efficient Actin Promoter for Use in Rice Transformation" Plant Cell, vol. 2, pp. 163-171, 1990.

Meyer, et al. "Homology-Dependent Gene Silencing in Plants" Annu. Rev. Plant Physiol. Plant Mol. Biol, Vo. 47, pp. 23-48, 1996.

Mitra, et al. "The *Chlorella* Virus Adenine Methyltransferase Gene Promoter is a Strong Promoter in Plants" Plant Mol. Biol., vol. 26, pp. 85-93, 1994.

Odell, et al. "Identification of DNA Sequences Required for Activity of the Cauliflower Mosaic Virus 35S Promoter" Nature, vol. 313, p. 810-812, 1985.

Park, et al. "Gene Silencing Mediated by Promoter Homology Occurs at the Level of Transcription and Results in Meiotically Heritable Alterations on Methylation and Gene Activity" Plant J, vol. 9, pp. 183-194, 1996.

Raines, et al. "A Novel Proline-Rich Protein From Wheat" Plant Mol. Biol., vol. 16, pp. 663-670, 1991.

Rathus, et al. "Effects of Promoter, Intron and Enhancer Elements on Transient Gene Expression in Sugarcane and Carrot Protoplasts" Plant Mol. Biol., vol. 23, pp. 613-618, 1993.

Roach "Nobilisation of Sugrcane" Proc Int. Soc. Sugarcane Technology, vol. 14, pp. 206-216, 1972.

Siebertz, et al. "Cis-Analysis of the Wound-Inducible Promoter wun1 in Transgenic Tobacco Plants and Histochemical Localization of its Expression" Plant Cell, vol. 1, pp. 961-968, 1989.

Sleet, et al. "Studies on the Mechanism of Translational Enhancement by the 5'-leader Sequence of Tobacco Mosaic Virus RNA" Eur J. Biochem, vol. 175, pp. 75-86, 1988.

Smirnyagina, et al. "Translational Efficiency and Competitive Ability of mRNAs with 5'-Untranslated Alpha Beta-Leader of Potato Virus X RNA" Biochimie., vol. 73, pp. 587-598, 1991.

Soares "Construction of Directional cDNA Libraries" Automated DNA Sequencing and Analysis, pp. 110-114, 1994.

Srivastava, et al. "Quantitative Analysis of the Effect of Selection History on Sugar Yield Adaptation of Sugarcane Clones" Theoretical & Applied Genetics, vol. 87, pp. 627-640, 1994.

Tanaka, et al. "Enhancement of Foreign Gene Expression by a Dicot Intron in Rice But Not in Tobacco is Correlated with an Increased Level of mRNA and an Efficient Splicing of the Intron" Nucleic Acids Res, vol. 18, pp. 6767-6770, 1990.

Tomashevskaya, et al. "Effects of Sequence Elements in the Potato Virus X RNA 5' Non-Translated Alpha Beta-Leader on its Translation Enhancing Activity" J Gen Virol, vol. 74, pp. 2717-2724, 1993.

Topfer, et al, "Expression Vectors for High-Level Gene Expression in Dicotyledonous and Monocotyledonous Plants" Methods Enzymol., vol. 217, pp. 66-78, 1993.

Voinnet, et al. "Systemic Spread of Sequence-Specific Transgene RNA Degradation in Plants is Initiated by Localized Introduction of Ectopic Promoterless DNA" Cell, vol. 95, pp. 177-187, 1998.

Wang, et al. "Characterization of Cisacting Elements Regulating Transcription From the Promoter of a Constitutively Active Rice Actin Gene" Mol. Cell Biol., vol. 12, pp. 3399-3406, 1992.

Williams, et al. "Chemical Regulation of *Bacillus thuringiensis* Delta-Endotoxin Expression in Transgenic Plants" Bio/Tech, vol. 10, pp. 540-543, 1992.

Wilmink, et al. "Activity of Constitutive Promoters in Various Species From the *Liliaceae*" Plant Mol, Biol., vol. 28, pp. 949-955, 1995.

Zhang et al. "Analysis of Rice Act 1 5' Region Activity in Transgenic Rice Plants" Plant Cell, vol. 3, pp. 1155-1165, 1991.

PCT Search Report PCT/AU01/00418, mailed Jul. 5, 2001.

Dias "Analysis of Water Deficit Stress Responsive cDNA Clones and the Characterization of the Genomic Clone of Gene "Ip5" of Loblolly Pine (*Pinus taeda* L.)" Dissertation, Texas A&M, 143 Pages, 1995.

Elgar "Preparation of DNA From Hybridization Positive Phage" Plant Molecular Biology: a Laboratory Manual, Springer-Verlag, Berlin Heidelberg, pp. 113-114, 1997.

Yang, Meizhu "A Rapid and Direct Approach to Find Promoters for High-Level Gene Expression in Sugarcane" A Thesis Texas A&M, 104 Pages, 2000.

Chowdhury et al., "Molecular Analysis of Plants Regenerated from Embryogenic Cultures of Hybrid Suguarcane Cultivars (*Saccharum* spp.)", Theor Appl Genet., 86:181-188, 1993.

Kim, Y et al., "A 20 nucleotide upstream element is essential for the nopaline synthase (nos) promoter activity", Plant Mol. Biol., 24(1): 105-17, Jan. 1994.

Legaz et al., "Separation of soluble glycoproteins from sugarcane juice by capillary electrophoresis", Analytica Chimica Acta, 372: 201-208, 1998.

Wilcox et al., "Production and Purification of an Active Bovine Lysozyme in Tobacco (*Nicotiana tabacum*): Utilization of Value-Added Crop Plants Traditionally Grown Under Intensive Agriculture", J. Agric. Food Chem., 45:2793-2797, 1997.

Wilkie G.S. et al., "Regulation of mRNA translation by 5'- and 3'-UTR-binding factors", Trends Biochem Sci.; 28(4):182-8, Review, Apr. 2003.

Yang, Meizhu, et al.; "Genomics, Molicular Genetics & Biotechnology: A Rapid and Direct Approach to Identify Promoters that Confer High Levels of Gene Expression in Monocots", Crop Science, vol. 43, pp. 1805-1813, Sep.-Oct. 2003.

EMBL database. Accession No. AJ130830, "*Zea mays* gene encoding putative cell wall protein", May 13, 2000.

EMBL database. Accession No. AJ234401, "*Hordeum vulgare* partial mRNA", Jan. 7, 2000.

EMBL database. Accession No. AF221552, "*Oryza sative* prolinrich protein RiP-15 mRNA", Feb. 9, 2000.

EMBL database. Accession No. Y17332, "*Zea may* mRNA for proline-rich protein", Jun. 25, 1999.

EMBL database. Accession No. X52472, "*T. aestivum* mRNA for a proline-rich protein" Sep. 12, 1993.

```
1/1                                             31/11
AAG CCG GAA CCT CAG CCC CAG CCA GAA CCT TTG CCA AAA CCT GAG CCT CAG CCT AAG CCC
 K   P   E   P   Q   P   Q   P   E   P   L   P   K   P   E   P   Q   P   K   P
61/21                                           91/31
ACG CCC AAA CCA GAG CCA AAG CCC AAA CCA GAG CCG GTG CCC AAG CCT AAG CCT GAA CCA
 T   P   K   P   E   P   K   P   K   P   E   P   V   P   K   P   K   P   E   P
121/41                                          151/51
AAA CCT GAA CCA GAG CCT AAA CCT CAC CCT AAA CCA GAA CCA AAA CCT GAG CCT GAG CCT
 K   P   E   P   E   P   K   P   H   P   K   P   E   P   K   P   E   P   E   P
181/61                                          211/71
GAG CCA AAG CCG GAA CCA AAA CCA GAG CCT AAG CCT GAG CCC AAG CCA GAA CCA AAA CCT
 E   P   K   P   E   P   K   P   E   P   K   P   E   P   K   P   E   P   K   P
241/81                                          271/91
GAA CCA CTG CCG AAA CCA GAG CCT CAA CCT GAG CCG AAA CCA GAA CCA AAA CCT GAA CCA
 E   P   L   P   K   P   E   P   Q   P   E   P   K   P   E   P   K   P   E   P
301/101                                         331/111
GTG CCG AAA CCA GAG CCT AAG CCT GAG CCC AAA CCA GAA CCA AAA CCC GAG CCT AAG CCA
 V   P   K   P   E   P   K   P   E   P   K   P   E   P   K   P   E   P   K   P
361/121                                         391/131
GAA CCA AAA CCC GAA CCA TTG CCG AAG CCT GAG CCT AAG CCA GAA CCA AAA CCC GAA CCA
 E   P   K   P   E   P   L   P   K   P   E   P   K   P   E   P   K   P   E   P
421/141                                         451/151
TTG CCG AAA CCA GAG CCT AAG CCT GAA CCC AAG CCG GAA CCA AAA CCT GAA CCA CTG CCG
 L   P   K   P   E   P   K   P   E   P   K   P   E   P   K   P   E   P   L   P
481/161                                         511/171
AAA CCA GAG CCT AAG CCT GAG CCC AAG CCA GAA CCA AAA CCC GAA CCA TTA CCG AAA CCA
 K   P   E   P   K   P   E   P   K   P   E   P   K   P   E   P   L   P   K   P
541/181                                         571/191
GAG CCT AAG CCT GAG CCT AAG CCA GAA CCA AAA CCC GAA CCA CTG CCG AAG CCA GAG CCC
 E   P   K   P   E   P   K   P   E   P   K   P   E   P   L   P   K   P   E   P
601/201                                         631/211
AAG CCT GGA CCA AAA CCC AAA CCA CTG CCC AAG CCT GAT CCC AAG CCT AAA CCA AAA CCC
 K   P   G   P   K   P   K   P   L   P   K   P   D   P   K   P   K   P   K   P
661/221                                         691/231
GAA CCA CTA CCC AAA CCA GAG CCT GAA CCG AAG CCA AAG CCC AAG CCT GAA CCC AAA CCC
 E   P   L   P   K   P   E   P   E   P   K   P   K   P   K   P   E   P   K   P
721/241                                         751/251
AAA CCA GAG CCA AAG CCT GAA CCA AAA CCG GAG CCT GAG CCT GAA CCG AAG CCC GAG CCT
 K   P   E   P   K   P   E   P   K   P   E   P   E   P   E   P   K   P   E   P
781/261                                         811/271
GAG CCA AAA CCG GAA CCC AAA CCA GAG CCT AAG CCT GAA CCG AAG CCA GAG CCT AAG CCC
 E   P   K   P   E   P   K   P   E   P   K   P   E   P   K   P   E   P   K   P
841/281                                         871/291
GAG CCA AAA CCA GAA CCT AAA CCA AAA CCA AAG CCA GAG CCC CAA CCA AAA CCG GAG CCT
 E   P   K   P   E   P   K   P   K   P   K   P   E   P   Q   P   K   P   E   P
901/301                                         931/311
AAG CCC CAA CCA AAA CCT GAG CCC GAA CCC AAG CCT GAG CCC AAA CCA AAG CCC GAC CCG
 K   P   Q   P   K   P   E   P   E   P   K   P   E   P   K   P   K   P   D   P
961/321                                         991/331
CCG CAC ATC CCA CCG GCA GCT GAC AAC TGA TGA AGA GTC CAC TAG CCA TTA TAG CAG TAT
 P   H   I   P   P   A   A   D   N   *   *
1021/341                                        1051/351
CTG AAT AAA ATG CCC CAT GAG GCC GTA GTT GTA GCA TGC ATT TGC AGG TGC TAG CAG CTG
1081/361                                        1111/371
CTT GTT GTA CCT ATT CTT TCT GTG TTT GCG TCA TTT TTC TAT GTA ATG TTG ATT ACA TGA
1141/381
TTT TTA GTG CAA AAA AAA AAA AAA AAA AA
```

Fig. 3

```
  1 TAGACGCTACTCGGGCACTACCAACAGCTGCTCTAGAGAAAGAGAGAGAGGCAGAGAGCTAGCAACACACAGCAGAGA  80

81 GAGAGGCAGAGAGCTAGCC ATG GCG GCG CCG CGT CGC CTC TCT TGG TGC TGC CTT CTC TTC GCC 144
  1                     M   A   A   P   R   R   L   S   S   C   C   L   L   F   A   15

145 GTG CTT CTG GGA GCA GTG CTG GCC ACT GCC ACC GCC TTC TTC GAA CAA GCG GCG GCT GCC 204
 16  V   L   L   G   A   V   L   A   T   A   T   A   F   F   E   Q   A   A   A   A   35

205 GGC GTC GGG CTT GGT CAC GGC GCC CGT TTC GCG CGC AAG CAT GGA CGT GCT GCC GCC GAG 264
 36  G   V   G   L   G   H   G   A   R   F   A   R   K   H   G   R   A   A   A   E   55

265 CTG CCG CAG CCG GAG CCA CAA TTC AAA CCT GAA CCT AAG CCG GAA CCC CAG CCC CAG CCA 324
 56  L   P   Q   P   E   P   Q   F   K   P   E   P   K   P   E   P   Q   P   Q   P   75

325 GAA CCT TTG CCA AAA CCT GAG CCT CAG CCT AAG CCC ACG CCC AAA CCA GAG CCA AAG CCC 384
 76  E   P   L   P   K   P   E   P   Q   P   K   P   T   P   K   P   E   P   K   P   95

385 AAA CCA GAG CCG GTG CCT AAG CCT GAA CCA AAA CCT GAA CCA GAG CCT AAA CCT CAC CCT 444
 96  K   P   E   P   V   P   K   P   E   P   K   P   E   P   E   P   K   P   H   P  115

445 AAA CCA GAA CCA AAA CCT GAG CCT GAG CCC AAG CCG GAA CCA AAA CCA GAG CCT AAG CCT 504
116  K   P   E   P   K   P   E   P   E   P   K   P   E   P   K   P   E   P   K   P  135

505 AAG CCC AAG CCG GAA CCA AAA CCT GAA CCA CTA CCG AAA CCA GAG CCT AAA CCT GAG CCG 564
136  K   P   K   P   E   P   K   P   E   P   L   P   K   P   E   P   K   P   E   P  155

565 AAA CCA GAA CCA AAA CCC GAA CCA CT                                                590
156  K   P   E   P   K   P   E   P                                                  163
```

Fig. 4

```
-1857                                                                          ACTGTCCATCATCTATC -1841
-1840 GGTTCATTCATCCACGATTTGGCTTGCACAAGCCATACACTGCCGACCTAGCTCGTGTTTAGATGCAATTTTTTTTTACA -1761
-1760 AAATGCTCCTGTAGCACTTTTTTATTGTTATTTGGAAATTAGTGTCTAATCGTGAACTAATTAGGCTTAAAAGATTCATC -1681
-1680 TCGTGAATTTCATCTAAACTGTGTAATTAGTTTTATTTTTTATCTATATTTAATGCTTCATGCATGTGTCTAAAGATTCG -1601
-1600 ATGTGATGGGAAATATTGAAAATTTTTGCAAAATTTTTTGCATCTAAACTGAGCCCTACACCTCGGTCCCAGACCGTTCG -1521
-1520 TCGATGAATCTGGACAACTACCTGTCCAGATTTTTATTCCTATACCAACAGTTTTTTGAATGGAGGGAGTACGAAGTCGC -1441
-1440 CAGTACGTGTCCCTTTTAACCTGTAGTGATAAAACTGTGAATTTCTAGATAAACTTTTGGGATGAGGCCCTATTTATCTG -1361
-1360 GCTTATAATCCGTCTTATTTAGCTTGTTTTTTCAGCCGGAACAGTATTTTTCTCTCACAAAAAATCAGCCAACAGTGTTT -1281
-1280 TTCAGCCGGCTTATAAACTTTTGGGATGCAACCATTTTTGAACCACTTTTCTTTTTTTAACGTATTTTCTACCACTTTTC -1201
-1200 AACCACGCACTGACGCACGCTATGCATGTAATTCAACAAGTACTCTTATTACTTACTTTGTCTAATTGACTGGTTTACCA -1121
-1120 TCACCCTGGACCTGCAGGCAAAGCAAGATGTGGACACTGCCGTGTCGGTCACGCAGGAAATCAAAGTTCTACGACGACAT -1041
-1040 TTGTACGGCGCGGGTACGCATCTTAGCGTCCTCACTCTCATCTTCTCCGGCCAGCACAGCCGCAATACACGCACACACG -961
 -960 TACTCTCGGAACGGTCACTACACAGTCTGATGTGCTGCACCGTACGGCCTGCAATGCAACCATGCATATCATCGATCAT -881
 -880 GTGTCTCACAGTGCCGTCTGTGTCCTTTCCCTTAGGCGATCCTGATCTTGAGCTTCACGAGCTGAGTGCCCGCCAGCCAT -801
 -800 GCATGCATGATGTCCACCAGACATGCATGCATGGCACACCTAGCAGCTCGCCATGCATAGGACTAGCTAGCTATAGGACG -721
 -720 ATGATGATCTGAGCTCCATCCAGGACCATGTGCATGCAACAGCGCGGACAGATGAAGATGACAATTGCTAGCCTGGTCA -641
 -640 TCCATCGTCCACACAAAAATATCTTTGCTACCTCAAAGCAAGGAGGAAACCTACACAGATAACAACTGACTAGCCTGCAG -561
 -560 GGGATGAATCTTCATACATACTCCAGTACATAGCTCGCTCGCTGGTCATTTGGTCAACAGCGGCAGCATGCGTCGTCAAA -481
 -480 CACAAGCTAAATGCCTTTTACCCGTCCGTGTATCATCAAAAGTTAACAAACCTACCTGTCAGGCAGCAGCGTATATGTG -401
 -400 AAACAAGAAATGGATGGAAGAGTCCGTGAGAAAGTAAAGGTGAAAGATACGTGCTACTGCTATCCGTTGAATAGCAATAA -321
 -320 ACACGGGCTTAGCTGTTACCTACCCGTTGATACGGCGGAGGCCAAACGTGTAAAGCAGCTTATTTTTTTTAATGAGAGAG -241
 -240 TGTAAAGCAGCTACTTAGCTGGGCAGACAGCCCATCCACGCGTCCAAAGCTGCTTGGCTCTCGCGCGCTATAAATCCGAC -161
 -160 CCATGGCCACACCCCGTCATCCACATCCACACACACAACAGAGACTACTCGGGCACTACCAACAGCTGCTCTAGAGAAAG -81
  -80 AGAGAGAGGCAGAGAGCTAGCAACACACAGCAGAGAGAGAACTAGCAGGCGAACTTGTTGGAGGAGCAGGGCTAGCC -1
```

Fig. 6

```
  1 ATG GCG GCG CCG CGT CGA CTC TCT TCG TGC TGC CTT CTC TTC GCC GTG CTT CTG GGA GCA   60
  1  M   A   A   P   R   R   L   S   S   C   C   L   L   F   A   V   L   L   G   A   20

61 GTG CTG GCC ACC GCC ACC GCC TTC TTC GAC GAA GCG GCG GCT GCC GGC GTC GGG CTT GGC  120
 21  V   L   A   T   A   T   A   F   F   D   E   A   A   A   A   G   V   G   L   G   40

121 CAC GGC GCC CGT TTC GCG CGC AAG CAT GGA CGT GCT GCC GCC GAG CTG CCG CAG CCG GAG  180
 41  H   G   A   R   F   A   R   K   H   G   R   A   A   A   E   L   P   Q   P   E   60

181 CCA CAG CCC AAA CCT GAA CCT AAG CCG GAA CCT CAG CCC CAG CCA GAA CCT TTG CCA AAA  240
 61  P   Q   P   K   P   E   P   K   P   E   P   Q   P   Q   P   E   P   L   P   K   80

241 CCT GAG CCT CAG CCT AAG CCC ACG CCC AAA CCA GAG CCA AAG CCC AAA CCA GAG CCG GTG  300
 81  P   E   P   Q   P   K   P   T   P   K   P   E   P   K   P   K   P   E   P   V  100

301 CCC AAG CCT AAG CCT GAA CCA AAA CCT GAA CCA GAG CCT AAA CCT CAC CCT AAA CCA GAA  360
101  P   K   P   K   P   E   P   K   P   E   P   K   P   H   P   K   P   E  120

361 CCA AAA CCT GAG CCT GAG CCC AAG CCG GAA CCA AAA CCA GAG CCT AAG CCT GAG CCC AAG  420
121  P   K   P   E   P   E   P   K   P   E   P   K   P   E   P   K   P   E   P   K  140

421 CCA GAA CCA AAA CCT GAA CCA CTG CCG AAA CCA GAG CCT CAA CCT GAG CCG AAA CCA GAA  480
141  P   E   P   K   P   E   P   L   P   K   P   E   P   Q   P   E   P   K   P   E  160

481 CCA AAA CCT GAA CCA GTG CCG AAA CCA GAG CCT AAG CCT GAG CCC AAA CCA GAA CCA AAA  540
161  P   K   P   E   P   V   P   K   P   E   P   K   P   E   P   K   P   E   P   K  180

541 CCC GAG CCT AAG CCG GAA CCA AAA CCC GAA CCA TTG CCG AAG CCT GAG CCT GAG CCT AAG  600
181  P   E   P   K   P   E   P   K   P   E   P   L   P   K   P   E   P   E   P   K  200

601 CCA GAA CCA AAA CCC GAA CCA TTG CCG AAA CCA GAG CCT AAG CCT GAA CCT AAG CCG GAA  660
201  P   E   P   K   P   E   P   L   P   K   P   E   P   K   P   E   P   K   P   E  220

661 CCA AAA CCT GAA CCA CTG CCG AAA CCA GAG C                                         691
221  P   K   P   E   P   L   P   K   P   E                                           230
```

Fig. 6 (Continued)

Cutters: BanI HaeIII HinfI & MboI

Non-Cutters: ApaI BamHI BglI, BglII, Bsp106, BstXI, DraI DraII EcoRI EcorV HincII, HindIII HpaI KpnI NotI, PstI, SacI SacII SalI SmaI SpeI XbaI XhoI & XmaIII

```
1/1                                    31/11
CAC ATC AAC ATT GTG GTC ATT GGC CAT GTC GAC TCT GGC AAG TCG ACC ACC ACT GGC CAC
 H   I   N   I   V   V   I   G   H   V   D   S   G   K   S   T   T   T   G   H
61/21                                  91/31
CTG ATC TAC AAG CTT GGT GGT ATT GAC AAG CGT GTG ATC GAG AGG TTC GAG AAA GAG GCT
 L   I   Y   K   L   G   G   I   D   K   R   V   I   E   R   F   E   K   E   A
121/41                                 151/51
GCG GAG ATG AAC AAG CGT TCA TTC AAG TAT GCG TGG GTG CTT GAC AAG CTC AAG GCT GAG
 A   E   M   N   K   R   S   F   K   Y   A   W   V   L   D   K   L   K   A   E
181/61                                 211/71
CGT GAG AGA GGT ATC ACA ATT GAT ATC GCC CTG TGG AAG TTT GAG ACC ACC AAG TAC TAC
 R   E   R   G   I   T   I   D   I   A   L   W   K   F   E   T   T   K   Y   Y
241/81                                 271/91
TGT ACT GTC ATT GAT GCC CCT GGA CAC CGT GAC TTC ATC AAG AAT ATG ATC ACT GGT ACT
 C   T   V   I   D   A   P   G   H   R   D   F   I   K   N   M   I   T   G   T
301/101                                331/111
TCC CAG GCT GAC TGT GCT GTT CTT ATC ATT GAC TCC ACC ACT GGT GGT TTT GAG GCT GGT
 S   Q   A   D   C   A   V   L   I   I   D   S   T   T   G   G   F   E   A   G
361/121                                391/131
ATC TCC AAG GAT GGT CAG ACC CGT GAG CAT GCT CTC CTT GCT TTC ACA CTT GGA GTG AAG
 I   S   K   D   G   Q   T   R   E   H   A   L   L   A   F   T   L   G   V   K
421/141                                451/151
CAG ATG ATT TGC TGC TGC AAC AAG ATG GAC GCC ACC ACA CCC AAG TAC TCC AAG GCC CGT
 Q   M   I   C   C   C   N   K   M   D   A   T   T   P   K   Y   S   K   A   R
481/161                                511/171
TAT GAT GAG ATT GTG AAG GAA GTC TCT TCC TAC CTG AAG AAG GTT GGA TAC AAC CCT GAC
 Y   D   E   I   V   K   E   V   S   S   Y   L   K   K   V   G   Y   N   P   D
541/181                                571/191
AAG ATC CAC TTT GTT CCC ATC TCT GGT TTC GAA GGT GAC AAC ATG ATT GAG AGG TCC ACC
 K   I   H   F   V   P   I   S   G   F   E   G   D   N   M   I   E   R   S   T
601/201                                631/211
AAC CTT GAC TGG TAC AAG GGC CCC ACC CTG CTT GAG GCT CTG GAC TTG ATC AAT GAG CCA
 N   L   D   W   Y   K   G   P   T   L   L   E   A   L   D   L   I   N   E   P
661/221                                691/231
AAG AGG CCT TCA GAC AAG CCC CTG CGT CTC CCC CTT CAG GAT GTG TAC AAG ATT GGT GGT
 K   R   P   S   D   K   P   L   R   L   P   L   Q   D   V   Y   K   I   G   G
721/241                                751/251
ATT GGA ACT GTT CCT GTT GGG CGT GTT GAG ACT GGT GTC ATC AAG CCC GGT ATG GTG GTT
 I   G   T   V   P   V   G   R   V   E   T   G   V   I   K   P   G   M   V   V
781/261                                811/271
ACC TTC GGT CCC AGT GGC CTT ACT ACT GAG GTT AAG TCT GTT GAG ATG CAC CAT GAG GCT
 T   F   G   P   S   G   L   T   T   E   V   K   S   V   E   M   H   H   E   A
841/281                                871/291
CTC CAG GAG GCT CTT CCT GGT GAC AAC GTT GGC TTC AAC GTT AAG AAT GTT GCT GTG AAG
 L   Q   E   A   L   P   G   D   N   V   G   F   N   V   K   N   V   A   V   K
```

Fig. 9

```
901/301                              931/311
GAT CTG AAG CGT GGG TAT GTG GCC TCC AAC TCC AAG GAT GAC CCT GCC AAG GAG GCT GCT
 D   L   K   R   G   Y   V   A   S   N   S   K   D   D   P   A   K   E   A   A
961/321                              991/331
AGC TTC ACC TCC CAG GTC ATC ATC ATG AAC CAC CCT GGG CAG ATC GGC AAC GGC TAC GCC
 S   F   T   S   Q   V   I   I   M   N   H   P   G   Q   I   G   N   G   Y   A
1021/341                             1051/351
CCA GTG CTG GAC TGC CAC ACC TCA CAC ATT GCT GTC AAG TTT GCT GAG CTT GTT ACC AAG
 P   V   L   D   C   H   T   S   H   I   A   V   K   F   A   E   L   V   T   K
1081/361                             1111/371
ATT GAT AGG CGG TCT GGC AAG GAG CTT GAG AAG GAG CCC AAA TTC CTC AAG AAC GGT GAT
 I   D   R   R   S   G   K   E   L   E   K   E   P   K   F   L   K   N   G   D
1141/381                             1171/391
GCT GGT ATG GTG AAG ATG GTT CCC ACT AAG CCC ATG GTG GTG GAG ACC TTC TCT GAA TAT
 A   G   M   V   K   M   V   P   T   K   P   M   V   V   E   T   F   S   E   Y
1201/401                             1231/411
CCT CCT CTT GGT CGC TTT GCT GTG CGG GAC ATG AGG CAA ACG GTG GCT GTT GGA GTC ATC
 P   P   L   G   R   F   A   V   R   D   M   R   Q   T   V   A   V   G   V   I
1261/421                             1291/431
AAG AGT GTG GAG AAG AAG GAC CCA ACT GGA GCC AAG GTG ACC AAG GCT GCC GCC AAG AAG
 K   S   V   E   K   K   D   P   T   G   A   K   V   T   K   A   A   A   K   K
1321/441                             1351/451
AAA TGA GGT GTC TGG CTG GTT CTG TGT TTG CTT GGG GAT ACC TAG TGG GAG CTT AAA ATA
 K   *
1381/461                             1411/471
TCT CGT CTT GTT CAC GTT ATT GCT GTT ATT GCG TGA GCA ACT AAA CTG TGT TGG CAA TGT

1441/481                             1471/491
CTG TCT GGT CGA TTT AGT ACT GTT ATT TTC GTT GGT TAA AAC AAG GTT GCT ATT GAG ACT

1501/501                             1531/511
CGT TTC TGT TAT TTT ATA TCG AAC ATC GGG TGT GAG CCA TGC ATG GTT ATG AGT TTT GTT

1561/521
AAA AAA AAA AAA AAA AAA
```

Fig. 9 (Continued)

Cutters: ApaI BstXI DraII EcorV, HindIII & SalI
Non-Cutters: BamHI Bsp106, EcoRI KpnI NotI PstI SacI SacII SmaI SpeI XbaI XhoI & XmaIII

```
-620                                                                GTACTCCGCCAGCGCGGCGCCGTTCCTCCCTTTCTTTCCGCTGTGCTTTGAGCCTG -561
-560 TTTGTTGATCACTAGAATCTACTCGGGTTTGGTCGTTCAGTCATGCATGGAGACGACCCGATTCATCCACTGATTCTAATCA -481
-480 AGTGTTGTTCCGCCGCTCGCTACCCTCTATTTAGTGTCTATAGACTAGAATCCAGTTTCGCATTTACAACTGATTGTGAGCC -401
-400 ATAAATTATAACGTTGGGTGTGTTCTAGACTAGAATCAGTTTCCGATCTATGAATTCATTAGTGGCTGAGGCACTTAACTCT -321
-320 GTTTGTGTGTAAGAACTGAGCCGATTCAATGCTCGAGTACTAACAAGTTTCCTTCGCCTCGCTCAACTCAGTA -241
-240 TGTACTCCGTATATAAACTTGATTCAGTTTGCACTGATTCTCGGCCATAGATATATACGTTCGTTGTTCATTAGAT -161
-160 CCAGTTCCGATCTCGATTACCTCGCGTAGGGTACTTGCGTTTGAATTTCCGATTCTGTTGATTGTTTGATTACTTG -81
-80 GTTTATTCCATATATTTATTCTACGTGTTTTATCGCTATTTGAATTTGAATGTAAGCAGCACTGTAGCGTTCCCTTCCAGCC -1

1 ATG GGT AAG GAG AAG ACT CAC ATC AAC ATT GTG GTC ATT GGC ATC AAC TCT GAC AAG   60
  1  M   G   K   E   K   T   H   I   N   I   V   V   I   G   H   V   D   S   G   K  20

61 ACC ACC ACT GGC CAC CTG ATC TAC AAG CTT GGT GGT ATT GAC AAG CGT GTC ATC GAG  120
 21  T   T   T   G   H   L   I   Y   K   L   G   G   I   D   K   R   V   I   E  40

121 AGG TTC GAG AAA GAG CTC AAG GCC GAG CGT ATG AAC AAG CGT TCA TTC AAG TAT GCG TGG GTG CTT  180
 41  R   F   E   K   E   L   K   A   E   R   M   N   K   R   S   F   K   Y   A   W   V   L  60

181 GAC AAG CTC AAG GCC GAG CGT GAG GGT ATC ACA ATT GAT ATT GCC CTG TGG AAG TTT  240
 61  D   K   L   K   A   E   R   E   R   G   I   T   I   D   I   A   L   W   K   F  80

241 GAG ACC ACC AAG TAC TAC TGT ACT TCC CAG GCT GAC TGT GCT GAC CAC CGT GAC TTC ATC AAG  300
 81  E   T   T   K   Y   Y   C   T   S   Q   A   D   C   A   V   L   I   D   F   I   K  100

301 AAT ATG ATC ACT GGT TTT GAG GCT GGT ATC TTC AAG GAT GGT CAG ACC CGT GAG CAT GCT CTC CTT GCT  360
101  N   M   I   T   G   F   E   A   G   I   F   K   D   G   Q   T   R   E   H   A   L   L   A  120

361 GGT GGT TTT GAG GCT GGT ATC TTC AAG GAT GGT CAG ACC CGT GAG CAT GCT CTC CTT GCT  420
121  G   G   F   E   A   G   I   F   K   D   G   Q   T   R   E   H   A   L   L   A  140

421 TTC ACA CTT GGA GTG AAG CAG ATT TGC TGC AAC AAG GTAATGATTCCAGAATTTT  481
141  F   T   L   G   V   K   Q   I   C   C   N   K                              155
```

Fig. 11 (Continued)

```
 482 ATGTAGTCTGGTTCCTGATCTGATGGTGATTCCAGGAATTTACCTAGTCTGGTTCATGATCAGAGGTGCCTGTAAAT
 561 GTGTTTCAATAGTCTAGCAATTATTTATGCATTGCTTCAGTGTCTCAATTATACTTCAAGTTACTGTATTGGTTCT
 640 GATTAAATGCCTTATGTAAGCTATGTATACTAAATTGACAAATGAACACTGATTGCTTAAATTGAAAGGCATCTTCGT
 719 CCTATACATGTTAATGTATGATGCAACTTGTCTTCATTGCATAAATCTAATATGATTTTCCAGAGACAATTTTC
 798 CCAATGGGCGATTTAAATTTATGTTTCCACCTGATTTTAGAAATTGCTCGAGTAGTTGGATTGTGGAATACTTGCAA
 877 TGCATATGTAGTTGAAGCAAAAGGSTTTGCATAATTTAACTGTCTTCATATGATTGCAATTGTACTTAGTTACTTTG
 956 TCAATTATTATAGGATTTGATGGCATGAACCTGTAAGCTCTCGTATTTTTTTGTATACTTGCTTATAATTTTACAGC
1035 CCGCACTAGTTAGTATATGAATAAATTTGTTAAGTAATCTGCCTGGCGGTTATTCGTTGACCCCAAGAAATTCATG
1114 CCTTAAGCAAGTAGTTGGCCAGTAATTTTGATTATATGTGTTGCATTTTACTGTTGCTTGCCAGTTTATGTCA
1193 CCTTATCTCATTCAACTATTGCGTATTTTGGGTTTTGCTGTTTTTTACAG                      1240

1241          ATG GAC GCC ACC ACA CCC AAG TAC TCC AAG GCC CGT TAT GAT GAG ATT 1288
   1           M   D   A   T   T   P   K   Y   S   K   A   R   Y   D   E   I    16

1289 GTG AAG GAA GTC TCT TAC CTC AAG AAG GTT GGG TAC AAC CCT GAC AAG ATC CAC TTT 1348
 17   V   K   E   V   S   S   Y   L   K   K   V   G   Y   N   P   D   K   I   H   F    36

1349 GTT CCC ATC TCT GGA TTC GAA GGT GAC AAC ATG ATT GAG AGG TCC ACT AAC CTT GAC TGG 1408
 37   V   P   I   S   G   F   E   G   D   N   M   I   E   R   S   T   N   L   D   W    56

1409 TAC AAG GGC CCA ACC CTC GAG GCT TTG GAC CTT GAC CTT ATC AAT GAG CCG AAG AGG CCT TCA 1468
 57   Y   K   G   P   T   L   E   A   L   D   L   D   L   I   N   E   P   K   R   P   S    76

1469 GAC AAG CCC CTG CGG CTC CCC CTT CAG GAT GTG GTG TAC AAG ATT GGT GGT ATT GGA ACT GTT 1528
 77   D   K   P   L   R   L   P   L   Q   D   V   V   Y   K   I   G   G   I   G   T   V    96

1529 CCT GTT GGG CGT GTT GAG ACT GGT GTC ATC AAG CCC GGT ATG GTG GTT ACC TTC GGT CCC 1588
 97   P   V   G   R   V   E   T   G   V   I   K   P   G   M   V   V   T   F   G   P    116
```

Fig. 11 (Continued)

```
1589 AGT GGC CTT ACT ACT GAG GTT AAG TCT GTT GAG ATG CAC CAC GAG GCT CTC CAG GAG GCT  1648
 117  S   G   L   T   T   E   V   K   S   V   E   M   H   H   E   A   L   Q   E   A   136
1649 CTT CCT GGT GAC AAC GTT GGC TTC AAC GTT AAG GTT GCT GTG AAG GAT CTG AAG CGT       1708
 137  L   P   G   D   N   V   G   F   N   V   K   V   A   V   K   D   L   K   R       156
1709 GGG TAT GTC GCC TCC AAC TCC AAG GAT GAC CCT GCC AAG GAG GCT GCT AGC TTC ACC TCC   1768
 157  G   Y   V   A   S   N   S   K   D   D   P   A   K   E   A   A   S   F   T   S   176
1769 CAG GTC ATC ATC ATG AAC CAC CCT GGG CAG ATC GGC AAC GGC TAC GCC CCA GTG CTG GAC   1828
 177  Q   V   I   I   M   N   H   P   G   Q   I   G   N   G   Y   A   P   V   L   D   196
1829 TGC CAC ACC TCA CAC ATT GCT GTC AAG TTT GCT GAG CTT GTA ACC AAG ATT GAT AGG CGG   1888
 197  C   H   T   S   H   I   A   V   K   F   A   E   L   V   T   K   I   D   R   R   216
1889 TCT GGC AAG GAG CTT GAG AAG GAG CCC ATG GTG GTG GAA ACC TTC TCT GAA TAT CCT CCT CTT GGT  1948
 217  S   G   K   E   L   E   K   E   P   M   V   V   E   T   F   S   E   Y   P   P   L   G   236
1949 AAG ATG GTT CCC ACA AAG CCC ATG AGG CAA ACG GAC ATG AGG GAC AAG GTC ATC AAG AGT GTG GAG  2008
 237  K   M   V   P   T   K   P   M   R   Q   T   D   M   R   D   K   V   I   K   S   V   E   256
2009 CGC TTT GCT GTG CGG GAC ATG AGG CAA ACG GAC ATG AGG GAC AAG GTC ATC AAG AGT GTG GAG  2068
 257  R   F   A   V   R   D   M   R   Q   T   D   M   R   D   K   V   I   K   S   V   E   276
2069 AAG AAG GAC CCA ACT GGA GCC AAG GCT ACC AAG GTG ACC AAG GCT GCC AAG AAG AAA TGA GGTGTCT  2129
 277  K   K   D   P   T   G   A   K   V   T   K   A   A   K   K   K   *                        294
2130 GGCTGGTTCTGTGTTCTGCTTGGGGATACTAGTTGGGAGCTTAAAATATCTCGGTTATTGTCACGTTATTGTCTGTTATTG             2208
2209 TGAGCAACTAAACTGCTGGCTGGCAATGTTGCTCGTTGATTGTACTCTTATTATCGTTGGTTAAACCAGTTGCTA                  2287
2288 CGTTAAGACTGTTTCGTTTATTTTATATCGAACATCGGGTGTCACCCATGCATCGTTATGAGTTTGTTACTACCCTT                2366
2367 GTTGCAGTTGTGTGGCCTGTTACCTGTTTGCTTGATTCTAAACAGCATCGAATGATTCCTCGCCATACCTCGTCTGCTG              2445
2446 CGTTCAAATTCGATCGAATTCCTGCCCAAACCTGTCATCCTTGCGGTTCAATTTCCATGCATAAAAATCCTTTTT                   2524
2525 AATCTTAAAACTTGCCAATCGCATATTGAAGGATTTTTGATGAAAA                                                2570
```

METHODS AND CONSTRUCTS FOR PRODUCING TRANSGENIC PLANTS AND METHODS OF RECOVERING EXPRESSED PROTEINS

RELATED APPLICATIONS

This application is a continuation of U.S. application Ser. No. 11/558,247, filed Nov. 9, 2006, which is a continuation of U.S. application Ser. No. 10/257,157 filed Feb. 11, 2003, now U.S. Pat. No. 7,141,427 issued Nov. 28, 2006, which is a U.S. national stage application of International Application No. PCT/AU01/00418 filed Apr. 11, 2001 entitled "Regulatory Element from a Sugarcane Proline Rich Protein and Uses Thereof," which claims priority to U.S. Provisional Application Ser. No. 60/196,085 filed Apr. 11, 2000 entitled "Processing of Transgenic Sugarcane for the Recovery of High Value Proteins." The entire contents of each of these documents are incorporated herein in their entirety by reference.

Applicants additionally cross-reference U.S. application Ser. No. 10/119,992 filed Apr. 10, 2002 and published as US 2002/0162141, which claims priority to U.S. Provisional Application Ser. No. 60/282,784 filed Apr. 10, 2001.

FIELD OF THE INVENTION

This invention relates to the genetic engineering and processing of transgenic sugarcane for the recovery of high value proteins, and to molecular farming with transgenic gramineous crops.

BACKGROUND OF THE INVENTION

Sugarcane is one of the most important global crops with an estimated annual net value of $143 billion (FAO Statistics, 1996). Modern cultivated sugarcane (*Saccarum* spp, hybrids) belongs to the genus *Saccharum*, an interspecific hybrid between the domesticated species *Saccharum officinarum* and its wild relative *S. spontaneum*. Chromosome numbers of sugarcane cultivars range from 100 to 130 with approximately 10% being contributed by *S. spontaneum*.

Interspecific hybridization has led to a huge improvement in sugarcane breeding. It has solved some disease problems, increased biomass yield and sugar yield, and improved adaptability for growth under various stress conditions (Roach et al, 1972, Srivastava et al., 1994). The production of transgenic plants may provide another complementary method for sugarcane breeding. There are various transformation methods that have been developed. Transformation mediated by *Agrobacterium* has provided a reliable means of creating transgenic plants in many species. Particle bombardment (biolistics) and electroporation have proved to be another successful method with monocots, which are less susceptible to *Agrobacterium* than dicots. Sugarcane has reliable systems for both transient gene expression and production of transgenic plants. The most commonly used method for transformation of sugarcane is panicle bombardment combined with a herbicide resistance gene as a selectable marker (Gallo-Meagher and Irvine, 1993; 1996; Bower et al., 1992; 1996). Production of transgenic sugarcane plants by intact cell electroporation has also been reported (Arencibia et al., 1995). Recently, *Agrobacterium*-mediated transfer has been used successfully in sugarcane transformation (Endquez-Obregon et al., 1998; Arencibia et al., 1998).

In spite of reliable techniques for transformation, the expression level of a transgene is still of concern. A DNA construct or vector that drives very high levels of expression is critical in the production of transgenic plants. In general, a transgene vector consists of a very simple construct in which the gene of interest is coupled to a promoter derived from a plant, a virus or a bacterium. Some promoters confer constitutive expression (like ubiquitin and actin), while others may be tissue-specific, wound-inducible, chemically-inducible or developmentally regulated.

The CaMV35S promoter is a well known constitutive and active promoter in dicots, but much less so in monocots. A number of investigations have shown that promoters isolated from monocots show higher activity in monocot species, and that adding an intron between the promoter and the reporter gene increases transcription levels (Wilmink et al., 1995; Ruthus et al., 1993; Maas et al., 1991). The rice actin promoter Act1 (McElroy et al., 1991; Wang et al., 1992; Zhang et al., 1991) and the maize ubiquitin promoter Ubi (Christensen et al., 1992) achieved far better expression than CaMV35S in most monocots tested. Among promoters tested in sugarcane, the Emu promoter and the maize ubiquitin promoter showed better expression than CaMV35S promoter (McElroy et al., 1991; Gallo-Meagher et al., 1993; Rathus et al., 1993). In contrast to cereal crops, in monocots such as tulip, lily and leek, the activities of the monocot promoters were much lower and did not significantly exceed the activity of the CaMV35S promoter. In dicots, the ubiquitin promoter also showed weaker activity than the CaMV35S promoter (Callis et al., 1990; Mitra et al., 1994). Variation in transgene expression levels between different species and promoters may be due to transcription factors, recognition of promoter sequences or intron splicing sites (Wilmink et al., 1995) or other factors. So far, no one has reported the use of promoters or introns from sugarcane itself. Endogenous sugarcane promoters may drive higher levels of expression of transgenes or more stable expression compared to heterologous promoters.

Promoters currently used in monocot transformation are mostly derived from highly expressed genes, such as actin or ubiquitin. The abundance of mRNA can be due to copy number of the gene (GENES V, pp. 703) or to the strength of the promoter (Holtorf et al., 1995). There are no reports indicating what genes are most abundantly expressed in sugarcane, or the gene copy number for abundant messenger RNA in the sugarcane genome. The applicant describes herein newly identified promoters isolated from sugarcane which may prove useful in the expression in monocots of genes of interest.

SUMMARY OF THE INVENTION

In its broadest embodiment the present invention provides a method of identifying genetic elements useful for genetically engineering sugarcane or other monocots, to the transformation of the monocots with the genetic elements so that they produce a desired product, to regeneration of engineered plants for harvesting, and to purification of the desired product, such as a high value protein, from the regenerated plants. The invention also relates to novel ways to identify promoters useful for transformation of plants and to promoters identified according to the invention.

In one of the more general aspect, the invention disclosed herein provides a nucleic acid construct which may be inserted into the genome of any target plant. The construct use as a promoter a promoter isolated from sugarcane as disclosed herein.

Accordingly, in a first aspect, the present invention provides a nucleic acid construct for the expression of foreign genes in a plant, comprising a nucleotide sequence as shown in FIG. 3.

In a second aspect, the present invention provides a nucleic acid molecule, which encodes a promoter having a nucleotide sequence substantially as shown in FIG. 3.

In a third aspect, the present invention provides a nucleic acid molecule, which encodes a promoter having:

a) a nucleotide sequence as shown in FIG. 3; or b) a biologically active fragment of the sequence in a); or c) a nucleic acid molecule which has at least 75% sequence homology to the sequence in a) or b); or d) a nucleic acid molecule which is capable of hybridizing to the sequence in a) or b) under stringent conditions.

In a forth aspect, the present invention provides a transgenic plant stably transformed with a construct according to the invention.

Modified and variant forms of the constructs may be produced in vitro, by means of chemical or enzymatic treatment, or in vivo by means of recombinant DNA technology. Such constructs may differ from those disclosed, for example, by virtue of one or more nucleotide substitutions, deletions or insertions, but substantially retain a biological activity of the construct or nucleic acid molecule of this invention.

In a fifth aspect the invention provides a method of transforming sugarcane and regenerating said sugarcane using a reproducible biolistic-based transformation and regeneration system and the resulting plants cultured. High value protein and other materials are extracted from the harvested plants.

BRIEF DESCRIPTION OF THE DRAWINGS

FIG. 3 shows the nucleotide sequence and deduced amino acid sequence of the cDNA insert SPRP1.

FIG. 4 shows the 5' nucleotide sequence of SPRP2 and the deduced amino acid sequence.

FIG. 6 shows the 5' upstream and partial nucleotide sequence of SPRP gene.

FIG. 9 shows the cDNA sequence of EF1α.

FIG. 11 shows the DNA sequence of sugarcane EF1α genomic clone (4537 bp).

DETAILED DESCRIPTION OF THE PREFERRED EMBODIMENTS

Figure 1:
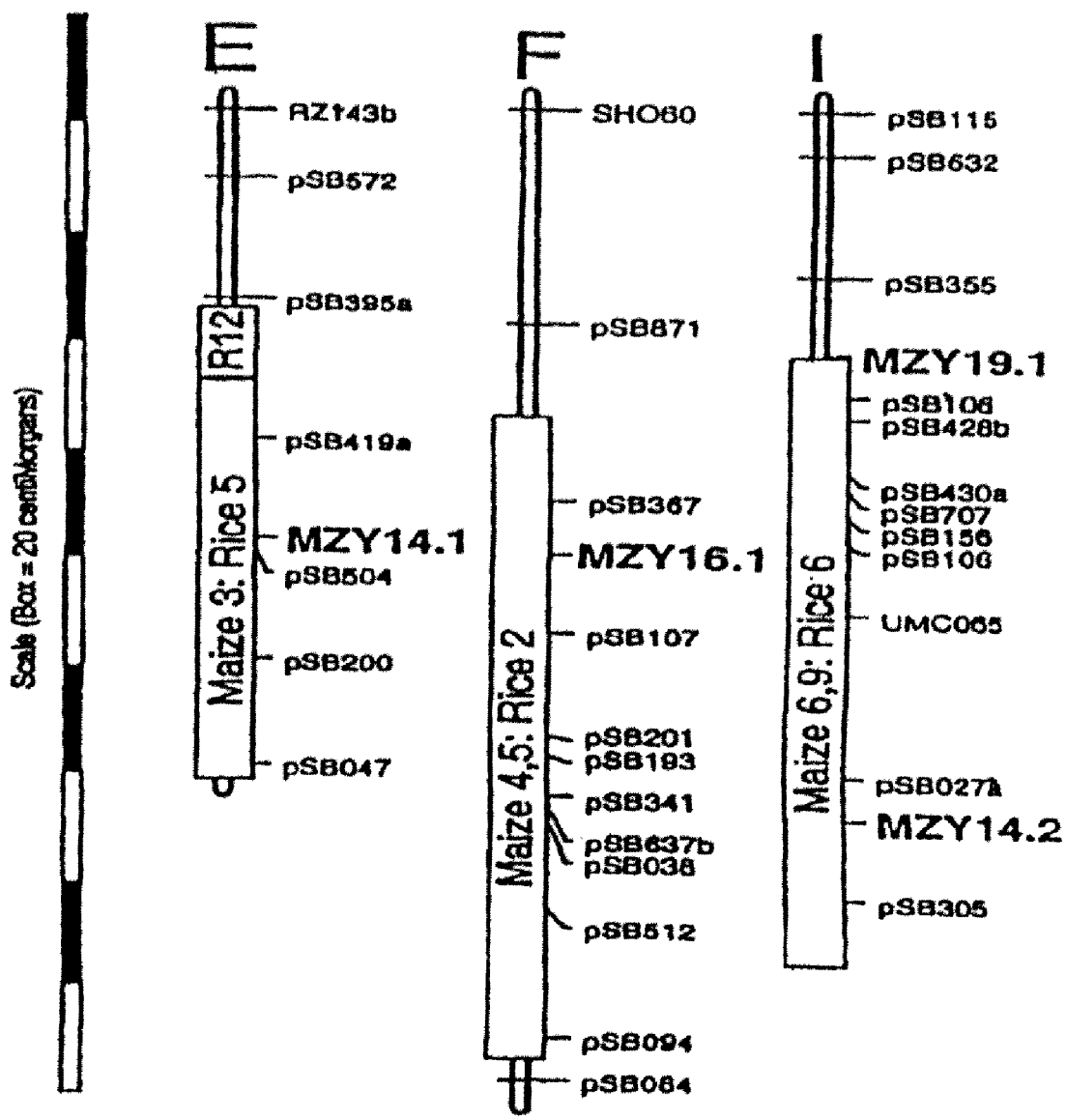
FIG. 1 shows a genetic map of highly-expressed sugarcane genes on the sorghum map.

The practice of the present invention employs, unless otherwise indicated, conventional molecular biology, microbiology, and recombinant DNA techniques within the skill of the art. Such techniques are well known to the skilled worker, and are explained fully in the literature. See, eg., Maniatis, Fritsch & Sambrook, "Molecular Cloning: A Laboratory Manual" (1982); "DNA Cloning: A Practical Approach," Volumes I and II (D. N. Glover, Ed., 1985); "Oligonucleotide Synthesis" (M. J. Gait, Ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture" (R. I. Freshney, Ed., 1986); "Immobilized Cells and Enzymes" (IRL Press, 1986); B. Perbal, "A Practical Guide to Molecular Cloning" (1984), and Sambrook, et al., "Molecular Cloning: a Laboratory Manual" $12^{th}$ edition (1989).

The description that follows makes use of a number of terms used in recombinant DNA technology. In order to provide a clear and consistent understanding of the specification and claims, including the scope given such terms, the following definitions are provided.

A "nucleic acid molecule" or "polynucleic acid molecule" refers herein to deoxyribonucleic acid and ribonucleic acid in all their forms, ie., single and double-stranded DNA, cDNA, mRNA, and the like.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus this term includes double-stranded DNA found, inter alia, in linear DNA molecules (eg., restriction fragments), viruses, plasmids, and chromosomes. In discussing the structure of particular double-stranded DNA molecules, sequences may be described herein according to the normal convention of giving only the sequence in the 5' to 3' direction along the non-transcribed strand of DNA (ie., the strand having a sequence homologous to the mRNA).

A DNA sequence "corresponds" to an amino acid sequence if translation of the DNA sequence in accordance with the genetic code yields the amino acid sequence (ie., the DNA sequence "encodes" the amino acid sequence).

One DNA sequence "corresponds" to another DNA sequence if the two sequences encode the same amino acid sequence.

Two DNA sequences are "substantially similar" when at least about 85%, preferably at least about 90%, and most preferably at least about 95%, of the nucleotides match over the defined length of the DNA sequences. Sequences that are substantially similar can be identified in a Southern hybridization experiment, for example under stringent conditions as defined for that particular system. Defining appropriate hybridization conditions is within the skill of the art. See eg., Sambrook et al., DNA Cloning, vols. I, II and III. Nucleic Acid Hybridization. However, ordinarily, "stringent conditions" for hybridization or annealing of nucleic acid molecules are those that (1) employ low ionic strength and high-temperature for washing, for example, 0.015M NaCl/0.0015M sodium citrate/0.1% sodium dodecyl sulfate (SDS) at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

Another example is use of 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with washes at 42° C. in 0.2×SSC and 0.1% SDS.

A "heterologous" region or domain of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (eg., a cDNA where the genomic coding sequence contains introns, or synthetic sequences having codons different than the native gene). Allelic variations or naturally-occurring mutational events do not give rise to a heterologous region of DNA as defined herein.

A "coding sequence" is an in-frame sequence of codons that correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide in vivo. A polyadenylation signal and transcription termination sequence will usually be located 3' to the coding sequence.

A "promoter sequence" is a DNA regulatory region capable of binding RNA polymerase in a cell and initiating transcription of a downstream (3' direction) coding sequence. A coding sequence is "under the control" of the promoter sequence in a cell when RNA polymerase which binds the promoter sequence transcribes the coding sequence into mRNA, which is then in turn translated into the protein encoded by the coding sequence.

For the purposes of the present invention, the promoter sequence is bounded at its 3' terminus by the translation start codon of a coding sequence, and extends upstream to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes, prokaryotic promoters contain Shine-Delgarno sequences in addition to the –10 and –35 consensus sequences.

A cell has been "transformed" by exogenous DNA when such exogenous DNA has been introduced inside the cell wall. Exogenous DNA may or may not be integrated (covalently linked) to chromosomal DNA making up the genome of the cell. In prokaryotes and yeast, for example, the exogenous DNA may be maintained on an episomal element such as a plasmid. With respect to eukaryotic cells, a stably transformed cell is one in which the exogenous DNA is inherited by daughter cells through chromosome replication. This stability is demonstrated by the ability of the eukaryotic cell to establish cell lines or clones comprised of a population of daughter cells containing the exogenous DNA.

"Integration" of the DNA may be effected using non-homologous recombination following mass transfer of DNA into the cells using microinjection, biolistics, electroporation or lipofection. Alternative methods such as homologous recombination, and or restriction enzyme mediated integration (REMI) or transposons are also encompassed, and may be considered to be improved integration methods.

A "clone" is a population of cells derived from a single cell or common ancestor by mitosis.

"Cell," "host cell," "cell line," and "cell culture" are used interchangeably herewith and all such terms should be understood to include progeny. A "cell line" is a clone of a primary cell that is capable of stable growth in vitro for many generations. Thus the words "transformants" and "transformed cells" include the primary subject cell and cultures derived therefrom, without regard for the number of times the cultures have been passaged. It should also be understood that all progeny might not be precisely identical in DNA content, due to deliberate or inadvertent mutations.

Vectors are used to introduce a foreign substance, such as DNA, RNA or protein, into an organism. Typical vectors include recombinant viruses (for DNA) and liposomes (for protein). A "DNA cloning vector" is an autonomously replicating DNA molecule, such as plasmid, phage or cosmid. Typically the DNA cloning vector comprises one or a small number of restriction endonuclease recognition sites, at which such DNA sequences may be cut in a determinable fashion without loss of an essential biological function of the vector, and into which a DNA fragment may be spliced in order to bring about its replication and cloning. The cloning vector may also comprise a marker suitable for use in the identification of cells transformed with the cloning vector.

An "expression vector" is similar to a DNA cloning vector, but contains regulatory sequences which are able to direct protein synthesis by an appropriate host cell. This usually means a promoter to bind RNA polymerase and initiate transcription of mRNA, as well as ribosome binding sites and initiation signals to direct translation of the mRNA into a polypeptide. Incorporation of a DNA sequence into an expression vector at the proper site and in correct reading frame, followed by transformation of an appropriate host cell by the vector, enables the production of mRNA corresponding to the DNA sequence, and usually of a protein encoded by the DNA sequence.

As embodied and broadly described herein, the present invention is directed to processing of transgenic sugarcane for the recovery of high value proteins.

The invention also relates to identification and utilisation of promoters useful in genetically engineering sugarcane plants, the use of sugarcane as an expression system, and to methods of genetic engineering and manufacturing of products, such as high value proteins, from transformed sugarcane. The invention also includes products, such as proteins, produced according to the invention. The invention further includes equipment for the genetic engineering and manufacturing of products, such as high value proteins, from the transformed sugarcane. The invention is not limited to sugarcane, but may be applied to other plants, such as sorghum.

Crop plants improved by the insertion of foreign genes constitutes one of the main goals of plant genetic engineering. The transgenic plant technologies developed in our laboratories are useful for development and commercialisation of molecular farming in transgenic grasses.

Plants can be viewed as small efficient factories that need only water, sunlight, minerals, and the right combination of additional genes to economically produce exactly what industry wants. Given the right genes, plants can be used as recombinant expression systems to produce large quantities of modified starches, valuable industrial oils, plastics, Pharmaceuticals, vaccines or enzymes for food processing and other industries.

Because of high biomass potential, multi-functional utility, existing processing plants and other features, sugarcane was identified as an ideal recombinant expression system. Transgenic sugarcane has been demonstrated to be an ideal system for continued development towards commercialisation of molecular farming. *Sorghum* is also a useful system. In addition to the fact that sugarcane produces more biomass per acre than any other annual crop, the following unique features make sugarcane a particularly useful recombinant expression system. 1) The per weight basis of protein in the extracted sugarcane juice is 0.2% and the remainder is mostly sucrose and water. The sucrose provides stabilisation of the heterologous protein. 2) Since the overall protein content is low, the starting material for purifying the recombinant protein is a simple mixture which will facilitate the purification process.

The heterologous genes we expressed in sugarcane produce bactericidal lytic peptides and proteins and insecticidal and antiviral lectins that have high value as antimicrobial pharmaceuticals or biopesticides. The large biomass produced by these crops, and the milling technology in place for sugarcane offered a unique situation to capture transgenically expressed proteins as value added products. Transgenic peptides and proteins would be expected in the normally discarded residue of the first processing step after milling, juice clarification. The large scale extraction and purification of these value added products from the normally discarded residue generated in the first step of the sugarcane milling process, and commercialisation of this technology will provide new worldwide markets for sugarcane producers. Furthermore, by combining the strengths of classical crop improvement and plant biotechnology in our laboratories, the invention provides avenues for crop gene manipulation for crop improvement. The transformation and extraction technology of the invention may be applied to a broad range of proteins and other plants, such as sorghum.

There are two main bottlenecks for improving crop plants by gene transfer. First, many useful genes have not been precisely identified. The second major bottleneck concerns the inability to regenerate plants from the cells into which the new genes have been transferred. These constraints have been overcome according to the invention. The invention provides a reproducible biolistic based transformation and regeneration system for creating transgenic disease and herbicide resistant sugarcane. Using the invention, sugarcane can be successfully transformed on a routine basis.

In one example, we transgenically expressed in sugarcane the cDNA coding for the snow drop lectin, a potent broad spectrum insecticidal and antiviral protein found in the bulb of the snow drop lily. This protein may have many potential uses in the biopesticide industry, but was mainly used as a proof of principal.

The volume and price at which these kinds of high value proteins can be produced will determine to what extent they will be available for use, Current production methods are too expensive to allow for widespread market penetration. The current commercial cost of the snow drop lectin is $10,000 per gram. Based on current expression levels (~1.0%) of heterologous protein being achieved in our transgenic sugarcane plants, we expect to be able to produce these proteins for as low as $100.00 per gram using sugarcane as a recombinant expression system. This production cost would allow for widespread penetration into new markets.

Using standard molecular biology techniques, the gene encoding the snow drop lectin was fused between the maize ubiquitin promoter (this promoter is a strong constitutive promoter in grasses) and the nopaline synthase transcriptional terminator in a high copy number plasmid. This construct was used in biolistic co-transformation experiments using the maize ubiquitin/nptII gene construct (resistance to the antibiotic geneticin) as the selectable marker. The initial sugarcane cultivar to be transformed was CP65-357 as it is easy to regenerate. Targets of embryogenic calli were produced by culturing immature flower inflorescence on tissue culture medium supplemented with 3 mg/l 2,4-D. These embryogenic calli were bombarded (using a helium driven particle inflow gun) with tungsten particles coated with the appropriate plasmid DNAs to provide 4 μg per shot. Plants were cultured on tissue culture medium supplemented with 3 mg/l 2,4-D and 45 mg/l geneticin. After 9 weeks, resistant calli were transferred to medium supplemented with 1 mg/l1 2,4-D and 45 mg/l geneticin to promote shoot regeneration. Shoots were subcultured every two-weeks on this medium for two months at which time they were placed on rooting medium containing 45 mg/l geneticin. Plants displaying well developed roots were screened for the presence and expression of the transgene by PCR, Southern and Western blot analyses. A set of the highest expressors were grown in the greenhouse, and then in the field. The transgenically expressed protein was purified from these transgenic plants using tissue extraction, differential ultrafiltration, and ion exchange HPLC. Small plots of these transgenic plants were field grown for the initial pilot plant scale processing experiments conducted using the pilot plant located at the sugar mill in Santa Rosa, Tex.

The next phase used the transgenic sugarcane plants developed in our laboratories to take the next step required for the commercialisation of molecular farming in transgenic grasses. This transformation and extraction technology could be applied to a broad range of plants and high value proteins or other compounds. The large scale extraction and purification of these value added products, and the commercialisation of this technology will provide new worldwide markets for novel products produced in transgenic sugarcane or other plants.

The molecular farming phase requires a non-destructive method for recovering high value proteins or peptides (i.e., pharmaceutical peptides) from transgenic sugarcane. In processing cane, the industry crushes the stalk to extract the juice, then washes the residue with water to complete the extraction. This mixture is then adjusted to pH 7.0 with lime and heated to 90° C., the flocculent is removed and the juice evaporated to syrup for crystallisation of the sucrose. We predicted that the transgenically expressed proteins of interest would be removed with the flocculent. Because of the complexity of the mixture that is being heated, we cannot predict the stability of the proteins in the processing routine. New technology for juice clarification developed in beet processing and now being adapted for cane processing enables the raw process material to be clarified without heating or liming. The process is micron filtration which removes high molecular weight materials from the juice and leaves a clear filtrate that contains the high value proteins. We then use this fraction for protein extraction and purification, For this, we constructed a pilot scale micron filtration unit coupled to ultramicron filtration and ion exchange chromatography units to separate the protein fraction of the juice and to prepare it for further purification.

Using transgenic sugarcane expressing the snow drop lectin (an insecticidal and antiviral protein), we have made six runs through the pilot plant.

The transgenic sugarcane is first shredded and crushed twice (without maceration water) in a pilot scale Squire mill. Essentially, the cane stalk is shredded and then pressed through 3 rollers on the Squire mill with 3,000 pounds per square inch. This produces a mixture of about 70% water, 15% sucrose, and 10% fibre. The remaining 5% of the mixture consists of proteins and other sugars, salts and organic molecules. The juice containing the high value protein is then pumped to a purification skid and filtered through a set of vibrating (self cleaning) screens and enters a tank. This step removes the fibre. The first screen is 150 microns, and the second is 100 microns. The pH of the juice is adjusted to 5.2 and it is supplemented with 1 mM EDTA and 0.1% sodium sulphite to prevent oxidation and the formation of phenolics. From the tank the juice is permeated through a 0.2 micron cross flow filtration membrane. This step removes all the insoluble solids and high molecular weight soluble solids such as bacteria, starches and dextrans. The permeate, which contains sugar and the high value protein, enters a second tank and the retentate in the first tank is discarded. From the second tank, the juice is permeated through a 0.05 micron membrane. This step removes soluble molecules with a molecular weigh greater than 150,000 kd. High value proteins with a molecular weight greater than 150,000 kd would be retained in the second tank, and could be further purified with the HPLC steps described below. The second permeate, which contains sugar and the high value proteins smaller than 150,000 W (snow drop lectin in this example) enters a third tank and the retentate in the second tank is discarded. At this point we have a relatively clean sample from which all high molecular weight material has been removed, i.e., bacteria, starch, dextrans, and proteins with high molecular weights.

From the third tank, the sample is further purified by 2 cycles of high pressure liquid chromatography (HPLC). The first cycle uses Dowex Mono 66 ion exchange resin, while the second cycle uses a hydrophobic interaction resin. Preliminary runs produced protein.

An additional step in the lab was added to obtain a highly pure protein. Further modifications can be made to address large volumes produced in the third tank. The first two membranes process the juice at 2 gallons per minute, but the HPLC can only handle 300 ml, per minute. We have identified low molecular weight out off membranes that can be used to concentrate the sample in the third tank. The water, sugars and other small molecules will flow through the membranes, but the high value protein will be concentrated in the third tank. This will greatly improve the performance of the HPLC steps. Further modifications using different initial extraction conditions, different ion exchange resins/membranes, affinity resins and HPLC columns can be used to enhance performance.

The initial pilot plant incorporated a Squire mill, piping and valves from the mill to the juice tank to the purification unit. Additional useful instrumentation which may be incorporated include pilot scale nano filtration (30,000 and 10,000 molecular weight cut-off) equipment, new HPLC columns and new ion exchange resins/membranes. This will greatly improve the performance and efficiency of the HPLC stops. The processing plants according to the invention described herein, or incorporating an ultramicron filtration unit coupled to a de-watering system, may be used to extract and purify transgenically expressed proteins, including such biologically active high value proteins as pharmaceutical proteins, biopesticides, and lytic peptides.

The invention allows for the rapid economic production of large quantities of high value proteins. Large amounts of transgenic plant material can rapidly be processed to produce large quantities of recombinantly expressed proteins, It is envisioned that this process could be used on any type of transgenic plant material to product essentially any type of protein. Slight modifications to the initial extraction maybe made for different types of starting materials, and the size exclusion of the molecular weight cut off membranes could be altered for each specific protein, as could be the final HPLC steps.

The following additional examples are offered to illustrate embodiments of the invention, and should not be viewed as limiting the scope of the invention.

Example 1

Development of Transgenic Grassps for Molecular Farming

This example relates to developing transgenic grasses suitable for molecular farming. Because of high biomass potential and multi-functional utility, sugarcane or sorghum may be used. The first step will be to introduce genes into these crops which will economically produce high value lytic peptides and proteins to be used in the pharmaceutical and biopesticide industries. Sugarcane and sorghum, closely related plants, are very efficient producers of biomass, and the sugarcane milling process is an efficient biomass extraction system. Transgenically expressed peptides and proteins would be expected in the normally discarded residue of the first processing step after milling, juice clarification.

Genetic transformation of grass-like crops has previously been slow because the methods of gene transfer that work for broadleaf plants are not suitable. We have developed a particle bombardment transformation system and a regeneration and screening technique which we used to produce transgenic sugarcane that is herbicide resistant. We have made significant progress in applying the technique to varieties of sorghum.

(For example, in connection with herbicide resistance and enhanced disease control, using a helium gun, sugarcane has been transformed with a UBI-bar construct and selected for resistance to bialophos.)

Using a herbicide resistance gene as a selectable marker for transformed plants, we will bombard embryogenic callus from sugarcane and sorghum with plasmid DNA containing sequences coding for lytic peptides. Expression of these cDNAs linked to the maize ubiquitin promoter will be assayed in transgenic plants by Northern and Western blots. Peptide activity will be estimated by tissue extraction, dialysis and bioassays. Transgenic plants will be field grown for preliminary processing experiments.

Example 2

Molecular Farming, with Transgenic Gramineous Crops

In this example, sugarcane and sorghum are also used to express lyric peptides and proteins that have high value as pharmaceuticals or biopesticides. As noted, we have developed a reproducible biolistic based transformation and regeneration system for creating transgenic herbicide resistant sugarcane (Gallo-Meagher and Irvine, 1993; 1995) and have made significant progress in biolistic transformation of sorghum. We have also obtained from industrial collaborators cDNAs that code for lytic peptides or proteins that have high value as pharmaceuticals or biopesticides, Specifically, this example relates to transgenically expressing in sugarcane and sorghum the cDNA coding for bovine lysozyme, a potent broad spectrum bactericidal protein found in cow rennin (Mirkov and Fitzmaurice, 1991). This protein has many potential uses in the biopesticide industry. For example, we have shown that the purified protein is extremely effective in decontaminating bacterial infested seed, is an effective topical agent for both prophylactic and curative uses, and that transgenic plants expressing bovine lysozyme are resistant to bacterial infection (Mirkov and Fitzmaurice, 1991). We have successfully expressed the cDNA for bovine lysozyme in tobacco, potato, tomato, and rice (Mirkov and Fitzmaurice, 1991). We also intend to express the cDNA coding for the Pepridyl MIM™ DEM C-1. We have obtained this gene from Demeter Biotechnologies, Ltd. They have demonstrated that this bio-compound is an effective antimicrobial against plant and animal diseases.

The volume and price at which these kinds of therapeutic proteins can be produced will determine to what extent they will be available for use. Current production methods are too expensive to allow for widespread market penetration. The cost of production of Peptidyl MIM™ can be as much as $10,000 per gram when produced synthetically, and bovine lysozyme has not been synthesised. In recombinant yeast expression systems, the cost of production ranges from a low of $2.00 per gram for certain Peptidyl MIM™ to $1,000 per gram for bovine lysozyme. Based on current expression levels of heterologous proteins being achieved in transgenic plants, we expect to be able to produce these proteins for as low as 0.5 cents per gram using sugarcane and sorghum as recombinant expression systems. This production cost would allow for widespread penetration into new markets. This proposed work relates directly to creating transgenic disease and insect resistant sugarcane.

Methodology

Using standard molecular biology techniques, the bovine lysozyme gene (Mirkov and Fitzmaurice, 1991) and the gene encoding the Peplidyl MIM™ DEM C-1 will be fused between the maize ubiquitin promoter (this promoter is a strong constitutive promoter in the Gramineae) and the nopaline synthase transcriptional terminator in a high copy number plasmid. This construct will be used in biolistic co-transformation experiments using the maize ubiquitin/bar gene construct (resistance to the herbicides Ignite and Herbeace) as the selectable marker (Gallo-Meagher and Irvine, 1993; 1995). The initial sugarcane cultivar to be transformed will be CP70-321 as it is the most widely grown cultivar in Texas, and is easy to regenerate. The grain sorghum variety Pioneer 8313 will be used initially as we have been able to generate embryogenic calli from floral meristems, have regenerated plants from this tissue, and it is widely grown in south Texas. Targets of embryogenic calli will be produced by culturing immature flower inflorescences on MS medium supplemented with 3 mg/l 2,4-D (Gallo-Meagher and Irvine, 1995). These embryogenic calli will be bombarded (using a helium driven particle inflow gun) with tungsten particles coated with the, appropriate plasmid DNAs to provide 4 pg per shot (Gallo-Meagher and Irvine, 1993; 1995). Plants will be cultured on MS medium supplemented with 3 mg/l 2,4-D and 5 mg/l Ignite. After four weeks, Ignite resistant calli will be transferred to MS medium supplemented with 1 mg/l 2,4-D and 5 mg/l Ignite to promote shoot regeneration (Gallo-Meagher and Irvine, 19953). Shoots will be subcultured every two weeks on this medium for two months at which time they will be placed on rooting medium containing Ignite (Gallo-Meagher and Irvine, 1995). Plants displaying well developed roots will be screened for the presence and expression of the transgene by PCR and Western blot analyses. A set of the highest expressors will be grown in the greenhouse. The transgenically expressed proteins will be partially purified from these transgenic plants using tissue extraction, dialysis, and differential ultrafiltration. The protein activity will be bioassayed using several species of plant pathogenic bacteria for the generation of kill curves. Further purification and bioassays will be carried out. Small plots of these transgenic plants will then be field grown for initial pilot plant processing experiments to be conducted using the pilot plant located at the sugar mill in Santa Rosa, Tex. Transgenically expressed peptides and proteins would be expected in the normally discarded residue of the first processing step after milling, juice clarification. This juice will be used as the starting material for partial purification and bioassays as described above.

Planned steps include:
Construction of the plasmids for transformations
Introduction into targets of sugarcane variety CP70-321 and sorghum Pioneer 8313
Tissue culture and regeneration of plantlets
Screening for the presence and the expression of the transgenes
Partial purification and bioassays
Field trials and initial pilot plant processing experiments Transgenic plants would be made available to growers immediately at the end of this study. The transgenic plants would then be processed in a normal fashion at the sugar mill to obtain the sugar. The normally discarded juice containing the value added peptides and proteins could then be purified further and the proteins and peptides marketed.

Example 3

Engineering Resistance to Sugarcane Mosaic Virus

Sugarcane mosaic virus (SCMV) and sorghum mosaic virus (SrMV) are aphid transmitted potyviruses with single stranded RNA genomes. There are several strains that cause significant losses in sugarcane growing areas throughout the world. These viruses have been difficult to control in cultivated varieties by the transfer of virus resistance genes from naturally resistant varieties through traditional breeding programs. However, it has now been demonstrated that it is possible to control potyviruses very effectively by genetic engineering. This technique is known as "coat protein-mediated resistance" and is a form of pathogen derived resistance. It has been demonstrated for many viruses, and in many plants, that the virus is controlled by transforming the plant with the virus gene that produces its coat protein. Furthermore, production of transgenic sugarcane is now a routine procedure in our laboratories.

A project has been initiated to produce transgenic sugarcane plants that express the coat protein gene of SrMV strain H, to produce resistance to this and other closely related strains of SCWV. This engineered resistance would be monogenic and, therefore, easily transferred to other sugarcane varieties by conventional plant breeding methods.

Example 4

Engineering Resistance to Sugarcane Mosaic Virus

Sugarcane mosaic was discovered in Louisiana by Brandes in the early part of the 20$^{th}$ century and the virus has evolved into different strains. Currently, Texas has one (strain H) of the world's 15 reported strains. Breeders found resistant varieties for early strains only to have them succumb to a new strain. This search and replace strategy has been the only source of mosaic resistance. However, it is now possible to control potyviruses, and the sugarcane mosaic virus (SCMV) is one, through coat protein-mediated resistance. Many plants have been given coat protein genes from viruses and have become resistant to the pathogen. The same strategy should work with sugarcane.

We have developed a technique for routinely inserting foreign genes into sugarcane. A collection of all SCMV strains available in the US has been established and the coat protein gene for SCMV strain H has been removed from the virus and its sequence determined.

We propose to use several plasmids with the SCMV-H coat protein and the UBI-bar selectable marker construct, and produce transgenic versions of Nco 310 and CP72-1210 that are resistant to sugarcane mosaic. The resistance engineered into these varieties could be transferred through conventional breeding.

Example 5

Control of Melon Diseases Using Transgenic Plant Technologies

Genetic engineering approaches may be used to incorporate disease and insect resistance genes into melon varieties, such as those important to southern Texas agriculture. This would allow a reduction in the amounts of pesticides currently being used, while maintaining or increasing production levels. Target genes include virus and whitefly resistance.

Example 6

Control of Plant Diseases and Insects and Other Desired Traits Using Transgenic Plant Technologies Using recombinant DNA technology, desired plant viral genes, and genes encoding lectins or lectin-like proteins, or bovine lysozyme, will be used to create constructs to allow for the desired expression in plants. These constructs will be utilised to create transgenic plants which will be evaluated for viral, bacterial, and insect resistance/immunity.

Example 7

Lambda Genomic Library Construction

For successful construction of a genomic library, the length of the starting DNA is very important. Fragments of DNA with one sheared end and one-restriction-enzyme-generated end compete for lambda DNA in the ligation reaction and decrease the formation rate of concatemers that can be packaged into bacteriophage λ particles. To avoid this problem, the length of starting DNA should be at least fourfold longer than the partial digestion products used to construct the library.

Young leaves of sugarcane cultivars, CP65-357 and CP72-1210 were cut into small pieces and wrapped with foil, frozen immediately in liquid nitrogen and then stored at −70° C. Genomic DNA (about 100 kb) was isolated from frozen leaves using a CTAB method (Honeycutt et al., 1992). This method yields good quality initial DNA when using fresh tissue, a wide-bore pipette and no shaking during preparation.

Sugarcane genomic DNA was partially digested with Sau3A1 (NEB). Restriction enzyme digestion conditions were optimised on a small scale before performing large-scale digestions of genomic DNA for preparation of a genomic library. In a small-scale reaction, 1 µg of genomic DNA was digested for 30 min with a serial dilution of Sau3A1 ranging in concentration from 0.0035-1 unit/50 µl reaction. The digested DNA was run on a 0.4070 agarose gel along with DNA markers (Lambda DNA/HindIII Markers). The gel was photographed, and the amount of enzyme needed to produce the maximum intensity of fluorescence in the size range from 15-23 kb was determined. Using the optimised conditions determined above, a large-scale reaction with 100 µg genomic DNA was carried out. The digested DNA was size fractionated by preparative agarose gel electrophoresis. DNA in the 10-23 kb range was cut out, digested with GELase (Epicentre Technologies, Madison W1) according to the manufacturer's protocol then precipitated with ethanol. The isolated DNA fraction was run on a 0.4% gel to confirm the size of genomic DNA.

The vector used for genomic library construction was Lambda Dash (Stratagene). The Lambda DASH II system takes advantage of spi (sensitive to P2 inhibition) selection. Lambda phages containing active red and gam genes are unable to grow on host strains that contain P2 phage lysogens. When an insert replaces the stuffer fragment, the recombinant lambda DASH II phage is able to grow on the P2 lysogenic strain. Therefore, by plating the library on the XL1-blue MRA (P2) strain, only recombinant phages are allowed to grow.

The fractionated DNA was ligated to Lambda DASH II/BamHI arms (Stratagene) at a ratio of 400 ng insert to 1 µg of arms in a total volume of 5 µl per reaction. The ligations were carried out at 16° C. overnight. The ligation solution was then packaged with both Gigapack III Gold packaging extract (Stratagene) and Packagene extract (Promega).

The packaged phages were plated on both XLI-Blue MRA and XL1-Blue MRA (P2) host strains after an appropriate dilution. The packaging efficiency of the Gigapack III Gold packaging extract (Stratagene) was slightly higher than the Packagene extract (Promega). The titers of packaging reaction are shown in Table 1. About $1 \times 10^6$ plaques were amplified and this amplified library was used for genomic library screening.

TABLE 1

COMPARISON OF TITERS (PFU/µg VECTOR) OF THE GENOMIC LIBRARY PLATED ON THE E. coli XL-1 BLUE HOST STRAIN WHEN USING DIFFERENT PACKAGING EXTRACTS

| E. coli Host strain | XL1-Blue MRA(P2) Test 1 | XL1-Blue MRA (P2) Test 2 |
|---|---|---|
| Gigapack III Gold packaging extract (Stratagene) | $1.62 \times 10^6$ | $2.06 \times 10^6$ |
| Packagene extract (Promega) | $1.25 \times 10^6$ | $1.60 \times 10^6$ |

Example 8

Initial Genomic Library Screening for Highly-Expressed Genes

Total RNA was isolated from leaves of sugarcane cultivar CP72-12 10 based on the method developed by Yang Si in Dr. Paterson's laboratory (pers. Comm.). About 1 g plant tissue was frozen in liquid nitrogen and ground into fine powder. This powder was then transferred into a 50 ml conical tube containing 10 ml ice-cold RNA extraction buffer (200 mM Tris-HCl pH 8.5, 2% SDS, 10 mM $Na_2$-EDTA, 1% Sodium deoxycholate and 1% polyvinyl pyrrolidone 40). The powder in solution was blended in a polytron at high speed for 1 min after adding 10 ml PCI (phenol:chloroform:isoamyl-alcohol=25:24:1). 0.45 ml of Sodium acetate (3.3M pH 5.2) was added to above solution and mixed well. This mixture was kept on ice about 15 min to let the RNA diffuse into the aqueous phase. The upper aqueous phase was separated by centrifugation at 3,500 rpm for 20 min and transferred to a fresh conical tube. The RNA was precipitated with an equal volume of isopropanol and 1/9 volume of 3.3M NaOAc (pH 6.1). The RNA pellet was rinsed with 70% (v/v) ethanol, and allowed to air-dry. The pellet was dissolved in 800 µl $H_2O$, mixed with 200 µl 10M LiCl and incubated an ice about 5-12 h. This solution was then centrifuged at 12,000 rpm for 15 min and the pellet was resuspended in 400 µl $H_2O$, and mixed with 600 µl 5M KOAc (pH not adjusted). The mixture was incubated again in ice for 3 h and centrifuged at 12,000 rpm for 20 min. In this step, the RNA pellet was freed of DNA and LiCl, and resuspended in 200 μl $H_2O$, then precipitated with ethanol. The RNA pellet was washed with 70% ethanol and vacuum dried for 3-5 min before being dissolved in 600 μl $H_2O$. The RNA was then ready for electrophoresis and column chromatography for Poly $A^+$ RNA isolation.

The quality of RNA preparation was checked by loading 1 μg of RNA on a 1% agarose gel in 1×TAE electrophoresis buffer, prepared in a RNase-free way. No high molecular weight bands (>20 kb) were visible (sign of DNA contamination) and rRNA bands were distinct under UV illumination.

Poly $A^+$ RNA was isolated from total RNA prepared above using Oligo (dT) Cellulose (NEB cat. #1401) according to the manufacturer's instructions. Twice-column-purified mRNA was then used for cDNA synthesis.

The poly $A^+$ RNA isolated above served as a template for synthesis of first strand cDNA by transcribing into first strand cDNA with BRL Superscript reverse transcriptase using oligo (dT) 12-18 as a primer. About 0.5-1 μg mRNA was first mixed with 0.5 μg Oligo (dT) 12-18, incubated at 70° C. for 10 min, and placed on ice for 2 min. The reverse transcription buffer, dNTP mix, $\alpha$-$^{32}$P dCTP and reverse transcriptase were then added to the above solution. The final reaction solution contained 20 mM Tris-HCl (pH 8.4), 50 mM KCl, 2.5 mM $MgCl_2$, 10 mM DT T, 0.3 mM each dATP, dGTP, dTTP and 2 μM dCTP and 9 μl of 6,000 Ci/Mol $\alpha$-$^{32}$P dCTP and 1 μl SuperScript II RT (200 units/μl, BRL). The reaction was incubated at 42° C. for 50 min, and the probe was denatured with 0.2N NaOH for 15 min. The denatured cDNA probe was added to hybridisation buffer for library screening.

For screening, it was important to maintain individual plaques (plaques should not touch each other) in order to clearly distinguish recombinants. The genomic library was plated on 100×15 mm petri dishes with NZY agar medium at a density about 5,000 plaques per plate. The plates were incubated at 37° C. for approximately 8-10 h, or until plaques were pinpoint-sized.

To harden the agarose, the plates were placed at 4° C. for at least 60 min prior to lifting. The Hybond-$N^+$ (Amersham) filters were labelled with water insoluble ink and progressively placed on the plates. To orient the filter to the plate, a 21-gauge needle (black ink attached) was stabbed through the filter into the agar asymmetrically at three points around the edge of the plate. The plaques were allowed to transfer for 3 min for the first lift and 5 min for the second lift. The filters were removed from the plates and placed plaque side up on a sheet of 3 MM paper.

The nylon filters were denatured after lifting by placing the membrane for 7 min on a pad of absorbent filter paper soaked in 1.5M NaCl and 0.5M NaOH. They were then neutralised an a pad of filter paper soaked in 1.5M NaCl and 0.5M Tris-HCl (pH 7.2) for 3 min and then repeated with a fresh solution. The membranes were rinsed for no more than 30 s by submerging the membrane in a 2×SSC solution and transferred to dry filter paper to air dry.

The phage DNA was fixed by placing the membrane on a pad of absorbent filter paper soaked in 0.4M NaOH for 20 min. The membranes were rinsed by immersion in 5×SSC with gentle agitation for no more than 1 min. The membranes were then hybridized with the $1^{st}$ strand cDNA probe. In total about 100,000 plaques were cultivated and screened with pooled $1^{st}$ strand cDNA probe.

Two steps were used in the first screening: In the first stage, $1\times10^5$ phages separated on 20 plates were screened by first strand cDNA to identify the clones with a strong hybridisation signal. Because some of clones with high signal might contain rDNA, or other highly repetitive sequences, further testing was needed. In the second stage, the same set of 20 filters were stripped and probed with poly A (−) RNA. The test result showed that most of the clones with a strong hybridisation signal did not hybridise with poly A (−) RNA. About 29 genomic clones which showed very strong hybridisation signals in the primary screening, but did not hybridise with poly A (−) RNA, were selected for secondary and tertiary screening. Only 12 clones showed very strong hybridisation signals under the secondary and tertiary screening, and were selected for further characterisation.

Example 9

Construction of cDNA Library

Poly A (+) RNA was isolated from leaf total RNA of sugarcane CP72-2086 using a Poly Quick mRNA isolation Kit (Stratagene) based on the manufacturer's protocol. Single strand and double stranded cDNA were produced from 5 μg poly A (+) RNA. The library was constructed in the Uni-ZAP XR vector (Stratagene). The primer was a 50-base oligonucleotide containing an XhoI restriction enzyme recognition site and an 18-base poly (dT). The poly (dT) region binds to the 3' poly (A) region of the mRNA template, and MMLV-RT begins to synthesise the first strand cDNA. The second strand cDNA was synthesised by RNase H and DNA polymerase I. Finally, EcoRI adapters were ligated with the termini of double-stranded cDNA, and XhoI digestion released the EcoRI adapter and residual linker-primer from the 3' end of the cDNA. The size-fractionated cDNA had an XhoI site at the 5' end and an EcoRI site at the 3' end. These cDNA inserts were ligated with EcoRI/XhoI double digested vector and packaged in Gigapack III Gold packaging extract. The packaged phages were plated on the *E. coli* cell line XL1-Blue MRF. About $1\times10^6$ primary clones were amplified and this amplified cDNA library was further screened by DNA probes.

Example 10

Purification of Lambda Phage DNA and Restriction Enzyme Mapping

The recombinant phage DNA of the twelve identified clones in Example 8 were purified from liquid lysates following a miniprep protocol (Elgar 1997). Briefly, 20 ml of liquid lysate was incubated with DNase I and RNase (final concentration 1 μg/ml) at 37° C. for 30 min. About ⅕ volume of PEG solution (3M NaCl, 30% PEG) was then added to the above solution and left on ice overnight. The above mixture was centrifuged at 10,000 rpm for 20 min. The pellet (PEG-phage complex) was resuspended in 400 μl STE buffer. An equal volume of 4% SDS was added and the solution incubated at 70° C. for 20 min. 400 μl 3M KOAc (pH 5.6) was subsequently added after cooling on ice for min. The resulting solution was centrifuged at 12,000 rpm for 10 min at 4° C. to remove debris. The supernatant was then precipitated with an equal volume of isopropanol, and the pellet resuspended in $H_2O$, and stored at −20° C.

The phage DNA from the selected 12 clones was digested with BamHI, EcoRI, and BamH1+EcoRI. These restriction enzymes were the cloning sites of the vector and did not cut the vector arms. The digestion was run on a 0.8% agarose Tris-borate-EDTA (TBE) gel. All 12 clones had three bands in common which were the left and right arms. The restriction digestion pattern for clone 9-1 and 9-2 was exactly the same. All the other clones showed different restriction fragment patterns.

To determine which fragments contained the coding region, a Southern blot was made from the gel. This Southern blot was hybridized with pooled first strand cDNA derived from poly A (+) RNA as described in Example 8. The fragments which hybridized with pooled cDNA contained the coding regions of highly expressed genes.

In order to determine whether any of the 12 clones contained ubiquitin genes, the above filter was stripped and hybridized with a subclone from the cDNA of p6t7.2bI (Christensen et al. 1992). The λ phage Southern blot analysis with ubiquitin cDNA probe indicated that λ phage clone 15-1 actually contained the ubiquitin gene (Data not shown).

The relative signal intensity of each lane, which may be related to abundance of the selected gene, can be revealed from the signal intensity-comparison between a selected clone and ubiquitin (ubi) genomic clone 15-1. The mRNA expression level of genes represented by clones 10-1 and 14-1 was much higher than ubi. Clones 9-1, 14-2, 16-1, 17-2, 18-1 and 19-1 probably contained genes with expression levels similar to ubi. Clones 8-1 and 21-1 had genes for which the expression level was lower than Ubi.

The 8 genomic clones 9-1, 10-1, 14-1, 14-2, 16-1, 17-2, 18-1 and 19-1 which had a similar or higher expression level, compared to ubi, were selected as probes for cDNA library screening. The restriction fragments of λ phage genomic clones containing the coding region served as probes to screen the sugarcane leaf cDNA library. About 10-20 cDNA clones were isolated from the sugarcane leaf cDNA library for each genomic clone. The hybridisation results showed that clones 10-1 and 14-1 contained the same gene. Also 14-2, 17-2 and 18-1 hybridized with same cDNA clones. So, in total, 5 different genes were found following the cDNA screening.

The recombinant cDNA inserts were converted to plasmids by in vivo excision according to Stratagene's protocol, leaving the cDNA inserts in the Bluescript SK plasmid vector with T3 and T7 promoters flanking the cDNA insert.

Briefly, the plaques of interest from the agar plate were transferred to individual sterile microcentrifuge tubes containing 500 µl of SM buffer and 20 µl chloroform and stored overnight at 4° C. or until used. The XL1-Blue MRF and SOLR cells were grown overnight in LB broth supplemented with 0.2% (w/v) maltose and 10 mM $MgSO_4$ at 30° C. The three components: 200 µl XL1-Blue MRF cells at an $OD_{600}$ of 1.0; 250 µl phage stock and 1 µl ExAssist helper phage (>1× $10^6$), were mixed in a Falcon 2059 polypropylene tube. The Falcon 2059 polypropylene tube was, incubated at 37° C. for 15 min, then 3 ml of LB broth was added and shaken at 37° C. for 2.5-3 h. The Falcon tube was heated at 68-70° C. for 20 min and spun at 1,000×g for 15 min. The supernatant contained the excised pBluescript phagemid packaged as filamentous phage particles and 1 µl of this supernatant was added to 200 µl of freshly grown SOLR cells at $OD_{600}$ 1.0. The cell mixture was incubated at 37° C. for 15 min and placed on LB-ampicillin agar plates and incubated overnight.

The cDNA insert were isolated by enzyme, digestion with EcoRI and XhoI, or by PCR.

All the cDNA clones were sequenced using T3 and T7 primers using the ABI Prism dRhodamine Terminator Cycle Sequencing Ready Reaction Kit. BLAST similarity searches based on partial sequences of both 5' and 3' of cDNA inserts indicated that 4 out of the 5 cDNAs clones were similar to known genes. Only one of them (14-2) did not show significant similarity with any genes in GenBank.

Techniques Used

Southern Blot Analysis

Ten µg of total genomic DNA isolated from sugarcane leaves (Honeycutt et al, 1992) was digested completely with restriction enzymes, electrophoresed on a 0.8% agarose gel overnight, and transferred to a Hybond N+ membrane (Amersham) in 0.4N NaOH for 24 h. The membrane was rinsed once with 2×SSC for 1 min. The membrane filters were prehybridised overnight at 65° C. with gentle agitation in prehybridisation solution containing 5×SSC, 5×Denhardt's solution, 0.5% (w/v) SDS and 50 µg/ml denatured herring sperm DNA. The DNA probes prepared for Southern blot analysis were based on random hexamer labelling. To carry out the labelling procedure, the DNA of interest was digested with an appropriate restriction endonuclease. The DNA fragment of interest was recovered by gel electrophoresis and GELase extraction (Epicentre Technologies) according to the manufacturer's protocol. The purified DNA fragments were denatured by boiling, annealed to random hexanucleotides, then incubated with Klenow fragment in a total volume of 50 µl solution containing 50 mM Tris-HCl (pH 8.0), 5 mM $MgCl_2$, 2 mM DT T, 20M (dATP+dTTP+dGTP), 0.2M HEPES (pH 6.6), 50 µCi 6,000. Ci/mmol [$\alpha$-$^{32}$P] dCTP and 1 µl Klenow. The reaction was carried out at 37° C. for 1 h and the labelled DNA was separated from unincorporated radioactive precursors by chromatography on a small Sephadex G-50 column. The purified probe after labelling was denatured by adding one volume of 0.4N NaOH for 15 min, and then added to hybridisation solution. The hybridisation box was incubated at 65° C. overnight in a shaker at 50 rpm.

Northern Blot Analysis 10-30 µg of total RNA isolated from root, stem and leaf of sugarcane were separated on a 1.2% formaldehyde/agarose gel containing 7% formaldehyde and 1×MOPS buffer. The gel was run in 1×MOPS buffer at 3-4 V/cm for 3 h or until the bromophenol blue band migrated approximately 8 cm. The RNA ladder was cut out, stained with ethidium bromide, and photographed under UV light to estimate the size of the RNA samples. The portion of the gel to be transferred to nitrocellulose was not stained, but placed in a large tray and rinsed several times with water to remove the formaldehyde. The RNA was transferred to a nylon membrane-Hybond N+ (Amersham) with 10×SSC and fixed by baking the filter for 2 h at 80° C. The membrane was hybridised with a cDNA probe. The procedure of prehybridisation and hybridisation was the same as the Southern hybridisation.

Sequencing of cDNA Clones

All cDNA clones selected from the cDNA library were in the pBluescript SK plasmid vector with T3 and T7 promoters flanking the cDNA insert. The cDNA clones were first sequenced using T3 and T7 primers and further sequencing by designing internal primers. The sequencing reaction was performed according to ABI PRISM dRhodamine Terminator Cycle Sequencing Ready Reaction kit and run on an ABI 377.

Subcloning and Sequencing of Lambda Genomic Clones Containing 5' Upstream Sequences A fraction of 5' cDNA which was about 100 bp in length, was used as a probe for hybridisation with Southern blot filters made from λ phage DNA digested with different enzymes. The fragments which were hybridised with the 5' end of the cDNA, were isolated and cloned into the pBluescript SK plasmid at the respective restriction sites. The positive subclones were confirmed by blue/white selection and restriction enzyme digestion. The subclones were further analyzed by sequencing.

Primer Extension and Manual Sequencing

The transcriptional initiation sites were determined by primer extension analysis according to the method developed by Dias (1995) with some modifications. Two 30-mer primers, both complementary to nucleotides near the translation start site, were synthesised and end-labelled with [$\gamma$-$^{32}$P] ATP and T4 polynucleotide kinase. Each labelled primer (1 pMol each) was annealed to 1 µg mRNA or 15 µg total RNA isolated from sugarcane leaves by heating to 65° C. for 5 min and incubating at 50° C. for 1 h. The annealed RNA/primer mixture was mixed with reverse transcription buffer in a total volume of 20 µl and then extended for 60 min at 50° C. using 200 U of Superscript reverse transcriptase II (Gibco BRL). The RNA was denatured by addition of 8 µl of 1N NaOH and incubation for 30 min at 50° C., neutralised with 5 µl of 3M sodium acetate pH 5.5, and precipitated by addition of 2 volumes of ethanol. The pellet was dissolved in 3 µl of TE buffer (pH 8.0) and 2 µl formamide stop solution. The primer-extended cDNA products were analyzed by electrophoresis on a 6% urea-polyacrylamide gel in parallel with a sequencing ladder generated with the same primer and corresponding genomic clone as template. Manual sequencing was conducted using Sequitherm Cycle Sequencing Kit (Epicentre Technologies, Madison, Wis.) with $\alpha$-$^{32}$PdATP.

Example 11

Mapping of Highly-Expressed Sugarcane Genes On the *Sorghum* and Sugarcane Genetic Maps Four of the five genes isolated could be mapped on an interspecific F2 cross between *S. bicolor* and *S. propinquum* (Chittenden et al. 1994). The PRP gene is located on linkage group E. AQ1 is located on linkage group F. The unknown clone 14-2 and EF1$\alpha$ gene are both located on linkage group I. The relative chromosomal locations in maize, rice and wheat were inferred and shown in FIG. 1.

Figure 2:
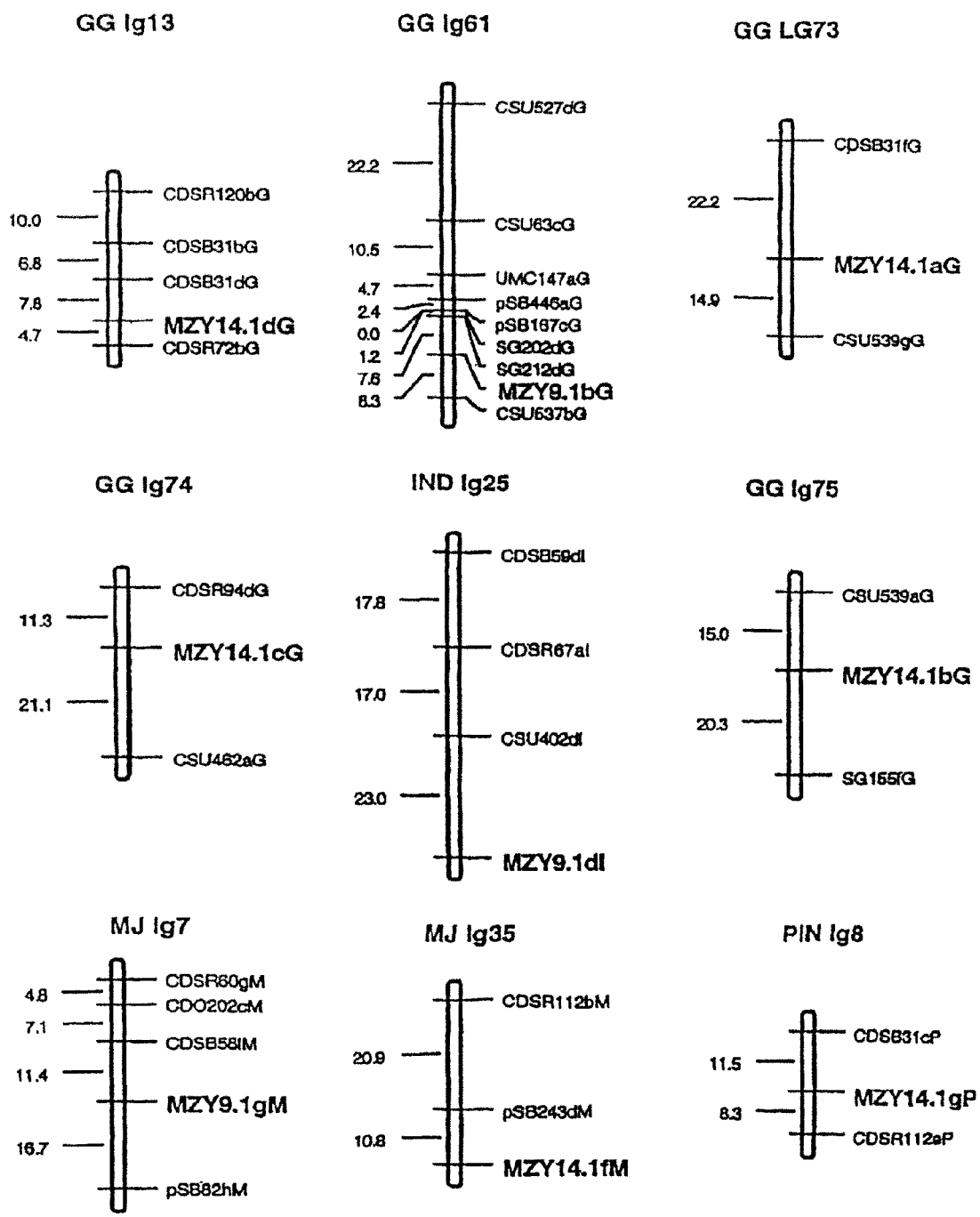
FIG. 2 shows a genetic map of highly-expressed sugarcane genes on the sugarcane map.

The sugarcane RFLP mapping were done in two interspecific F1 populations. They were derived from crosses between heterozygous parents: (1) 85 F1 plants from *S. officinarum* Green German (GG, 2n=97-117)×*S. spontaneum* IND 81-146 (IND, 2n=52-56); (2) 85 F1 plants from *S. officinarum* Muntok Java (M J, 2n=140)×*S. spontaneum* PIN 84-1 (PIN, 2n=96). Further details regarding the mapping population, as well as lab techniques, data analysis, and nomenclature for loci and "Linkage groups" are described by Ning et al., 1998. Two cDNA clones, MZY 9-1 (STUB) and MZY 14-1 (SPRP) detected restriction fragment length polymorphisms and fit 1:1 ratios. The map locations in sugarcane linkage groups are shown in FIG. 2. There are multiple loci for each probe. MZY 9-1 detected 3 loci and MZY 14-1 detected 6 loci.

Example 12 cDNA Clone and Genomic Clone of Sugarcane Proline-Rich Protein (SPRP1)

The first gene studied was the proline-rich protein (PRP). This gene showed an extremely strong signal when hybridised with pooled first strand cDNA. The proline-rich protein was highly expressed in leaf and stern, but expressed at low levels in roots. Calculation of the signal intensity using the Kodak ID image software indicated that the expression level of SPRP in leaf was about 20 times higher than in root and 3 times higher than in stem.

Figure 5:
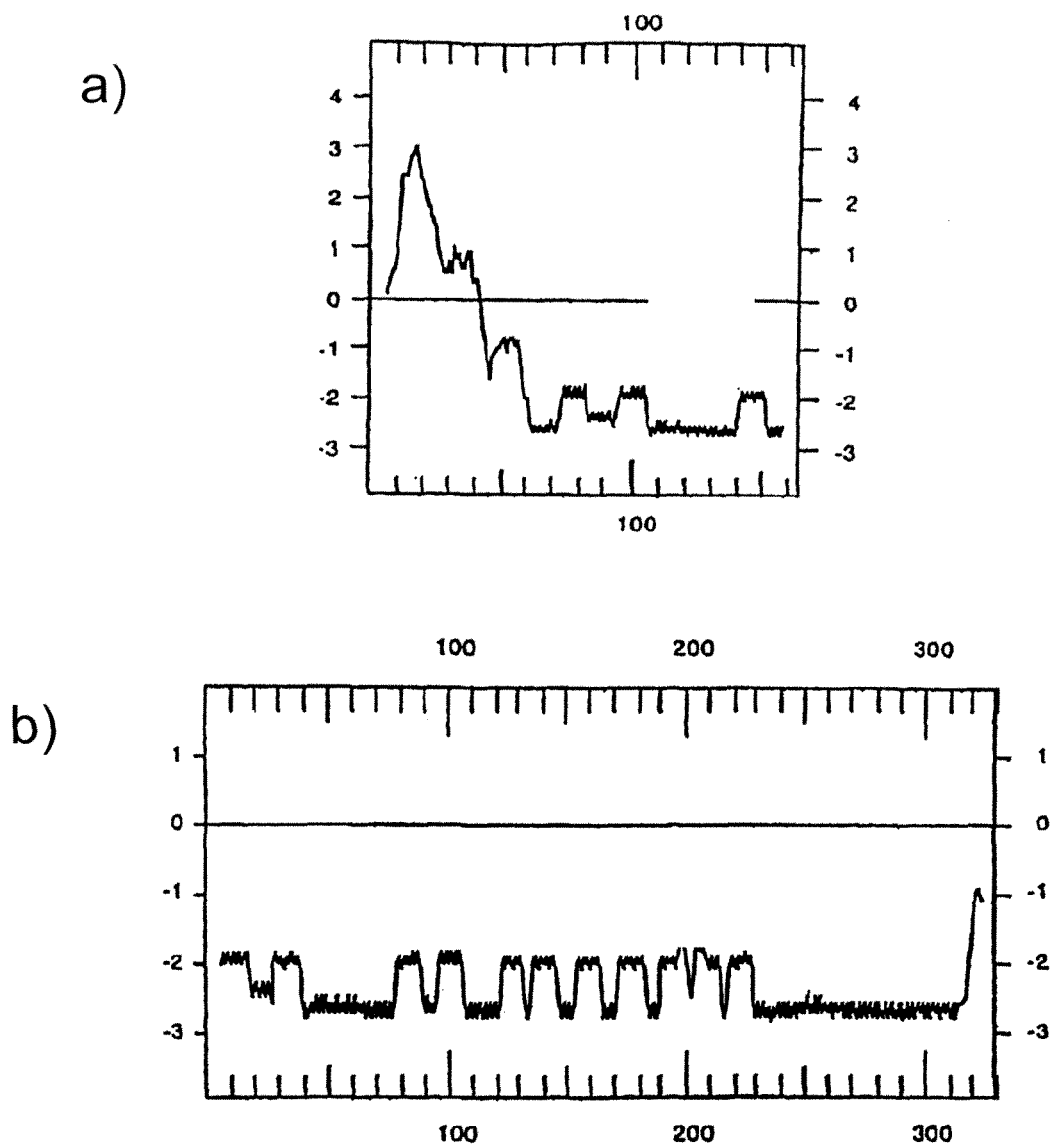
FIG. 5 shows the hydrophobicity plots of sugarcane proline-rich protein.

A cDNA clone SPRPI had an insert size of approximately 1.2 kb. This clone was initially sequenced. The nucleotide and deduced amino acid sequence is shown in FIG. 3. Both nucleotide and amino acid sequences have the greatest similarity to a maize proline rich protein (Accession number Y17332) and wheat proline-rich protein (Raines et al., 1991). A computer search of the nucleotide sequences in the GenBank database (July, 1999) revealed 73% identity between sugarcane and maize, and 70% identity between sugarcane and wheat. The comparison of the deduced amino acid sequences showed that sugarcane PRP has 78% similarity with maize and 77% similarity with wheat. The translation analysis showed that this cDNA clone was not full-length, lacking the 5' end but with 184 bp of 3' non-coding sequence. The predicted peptide sequence from this partial cDNA is shown in FIG. 4 and reveals that the peptide is very rich in proline (near 50%), lysine, and glutamic acid. It has a highly repetitive amino acid sequence in the middle of the peptide. The repeat unit PEPK also exists in the wheat proline-rich protein (Raines et al., 1991) and the maize proline-rich protein (accession number Y17332), The 5'-end sequence of SPRP was obtained from a longer cDNA clone (SPRP2). The 5' end nucleotide sequence of this longest cDNA from sugarcane together with its deduced amino acid sequence is shown in FIG. 4. This cDNA clone contains 99 bp of 5' non-coding sequence with one possible translation start site (ATG). As expected overlapping sequences were found between SPRP1 and SPRP2 cDNA. There was 93% nucleotide sequence identity between these two cDNA in 300 bp overlapping region. The hydrophobicity profile of both SPRP1 and SPRP2 deduced amino acid sequence is shown in FIG. 5. The sugarcane gene we isolated here has common structural features with the previously published wheat PRP sequence (Raines et al., 1991) and a maize proline-rich protein. It has a hydrophilic N-terminal region which is common to Pro-rich cell wall proteins (John and Koller, 1995), a high proline content, and is preceded by a hydrophobic signal peptide. This suggests that the SPRP protein may be a cell wall protein.

Figure 7:
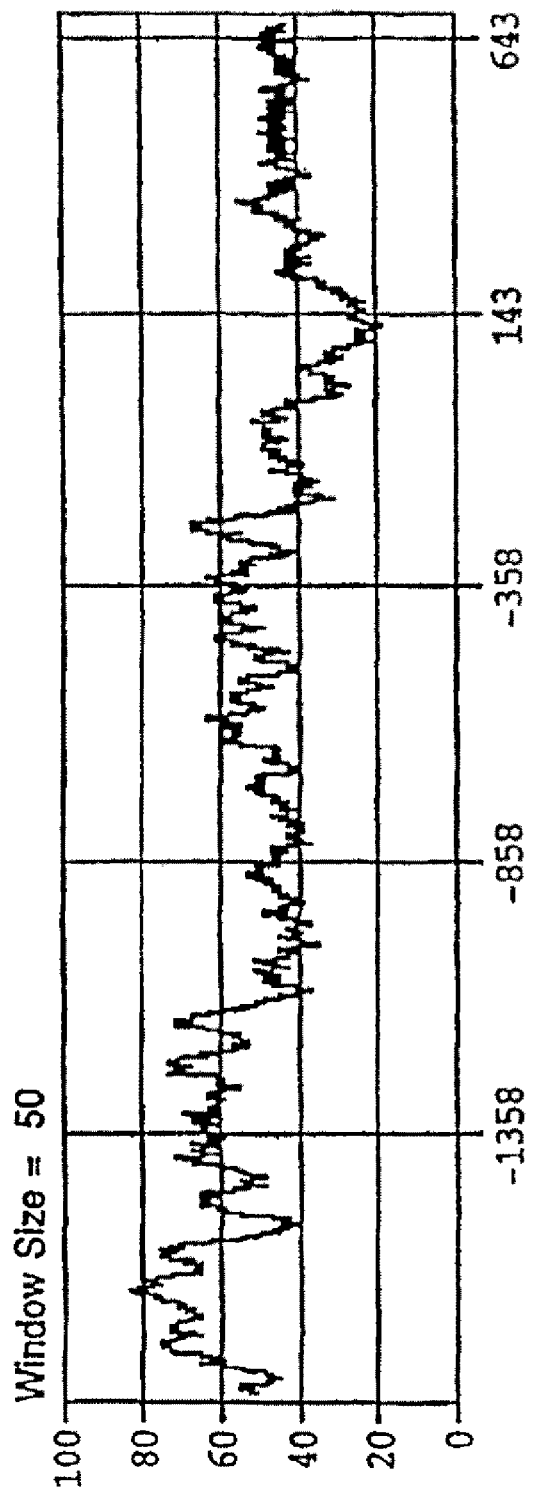
FIG. 7 shows the base composition of PRP genomic DNA sequence from −1857 to 691.

Four genomic clones (clone number 10-1, 14-1, 28-1 and 30-1) of the PRP genes were found by screening of the genomic library. Two clones were chosen for further subcloning and analysis. An 8.0 kb EcoRI fragment from genomic clone 10-1 and a 5.7 kb XboI fragment from genomic clone 30-1 were subcloned into the pBluescript SK plasmid vector. These genomic subclones were further sequenced. Partial sequencing results showed that the XbaI site was very close to the transcription start site. Therefore, the 5.7 kb XbaI subclone does not have the complete promoter of PRP. Detailed sequencing was done on the 8 kb subclone EcoRI fragment which contained both the promoter and coding region. A total of 1.7 kb, of upstream sequence from the translation start site of PRP was sequenced from this clone (FIG. 6). Sequence analysis revealed that the promoter contained several important cis-elements. There is a consensus TATAAA box 172 bp upstream from the translation start codon ATG. These results indicated that the deduced translation start site might actually function in vivo. A sequence (5'-CCATC) resembling a CAAT box was found 37 bp upstream of the TATA box. The base composition plot (FIG. 7) of promoter and 5' coding regions showed that some regions of the promoter are AT rich.

Figure 8:
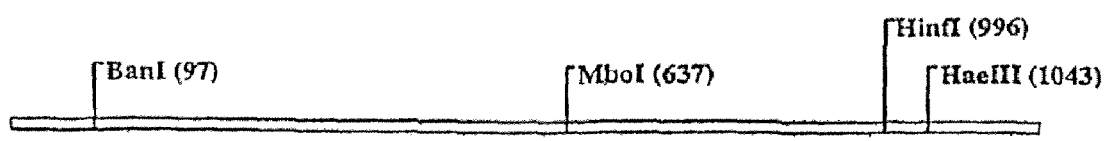
FIG. 8 shows restriction map of SPRP1.

Beside the previous Southern analysis among several varieties of sugarcane, another Southern analysis was performed for sugarcane hybrid CP65-357. There was no EcoRI, XbaI, BamHI or XhoI internal restriction sites in the 1.2 kb, PRP cDNA probe (FIG. 8). The number of bands in CP65-357 varied from 3 to 7 depending on which enzymes were used.

This suggested again that the SPRP might be a small gene family in the sugarcane genome.

Example 13

Figure 10:
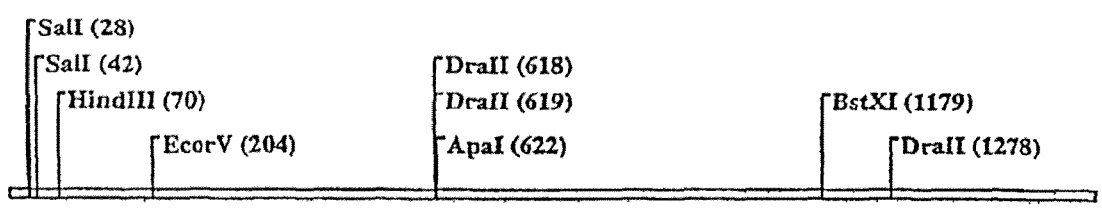
FIG. 10 shows restriction map of EF1α.
Figure 11:
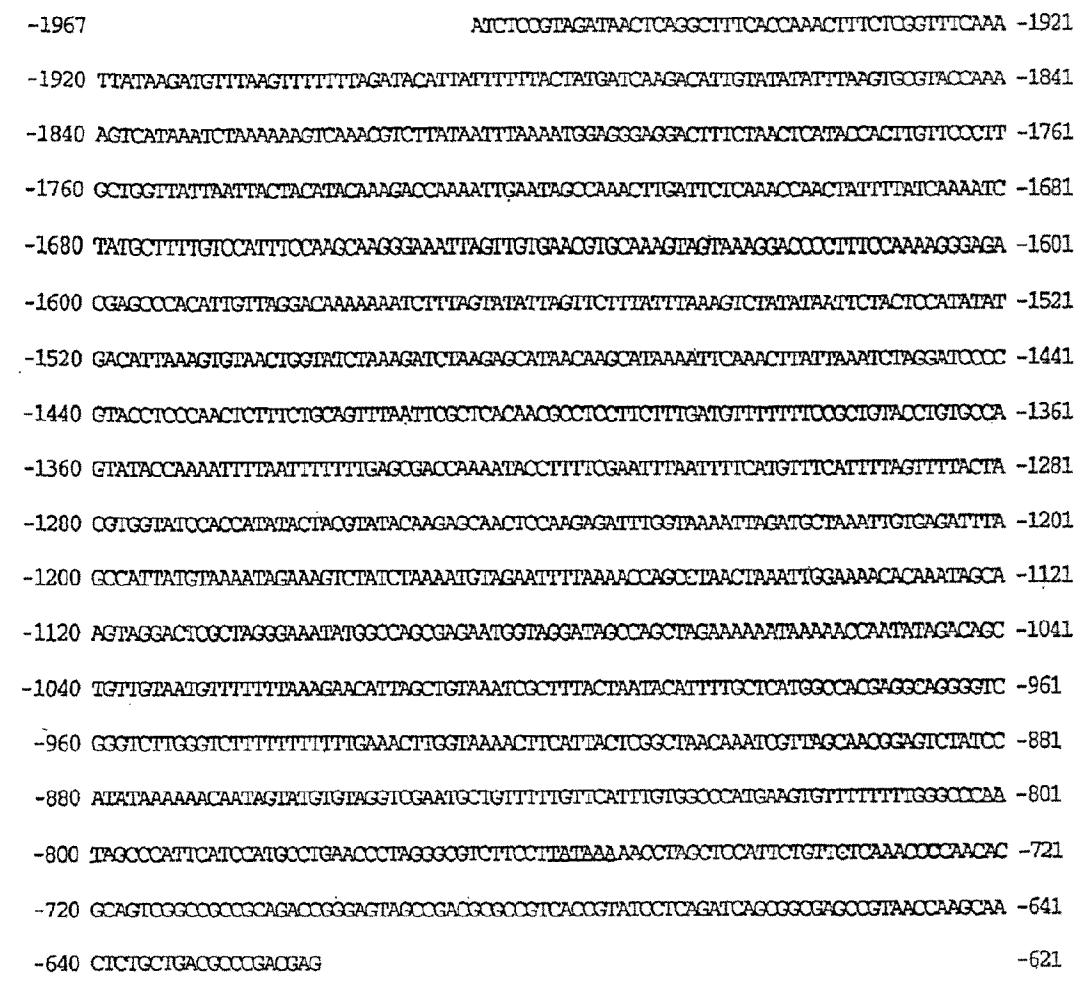
Figure 12:
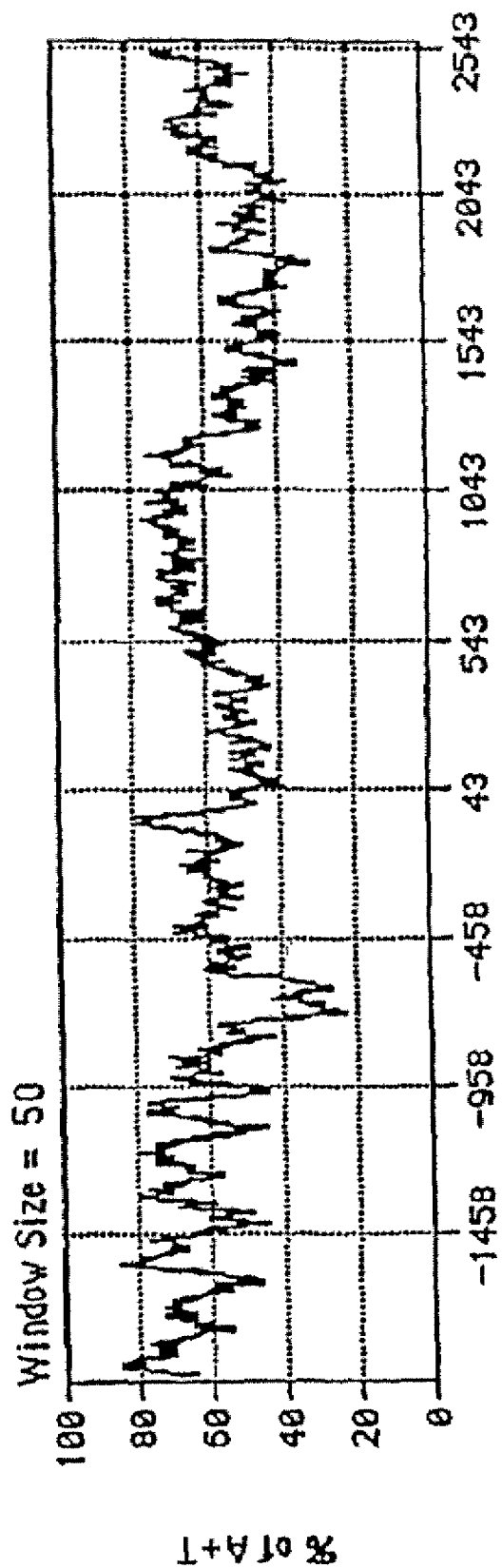
FIG. 12 shows the A and T base composition plot of SEF1α genomic DNA sequence from −1967 to 2570.

Isolation, Identification, and Characterisation of the Elongation Factor 1α (EF1α) Gene and its 5' Upstream Sequence Another interesting clone was elongation factor 1α. There are two reasons we chose this gene: First, the phage genomic clones of Southern blot with first strand cDNA indicated that the mRNA level of the EF1α was similar to that of ubiquitin. Second, the genomic clone we chose contained the entire coding region of elongation factor 1α based on the Southern blot analysis. Therefore, we isolated three cDNA clones after cDNA library screening with the EFIα genomic clone. One of them was a nearly full-length cDNA clone (1578 bp) and the 5' end of this cDNA was 18 bp down stream of ATG translation start size. This cDNA clone was named SEF 1α and its sequence is shown in FIG. 9. Homology search with the GenBank sequences revealed that the sugarcane EF 1α clone shows 93% identity to the maize nucleotide sequence and 99% identity or similarity to the maize deduced amino acid sequence (Berberich et al., 1995), respectively. The phage DNA of the EF1α genomic clone was digested with various restriction enzymes. The genomic insert in the phage clone was about 17 kb. The restriction map of the cDNA is given in FIG. 10 and most of the enzymes used (e.g. EcoRI and XboI) did not have sites in the coding region. The 9.5 kb EcoRI and 3.5 kb XbaI fragments from phage clone 19-1 were separately subcloned in the pbluescript SK vector. Genomic sequencing was done first on the genomic subclone containing a 3.5 kb XbaI fragment. This subclone contained the entire cDNA sequence, but the ATG translation start site of EF1α was located just 377 bp downstream from the XM cloning site. Therefore, a complete promoter region was not likely to be found in this subclone. So, another genomic subclone containing a 9.5 kb EcoRI fragment was used for sequencing of the 5' end of the untranslated leader sequence and promoter region. The 4,537 bp genomic sequence of the entire gene including the 5' upstream region is shown in FIG. 11. The genomic sequence matched base by base to the corresponding sugarcane and maize EF1α cDNA sequence (Accession number U7259). The comparison between genomic and cDNA sequences showed that there are two introns found. In the genomic clone one of them is located within the 5' non-coding region and is about 597 bp in length. There is a similar report in *Arabidopsis* AI EF1α gene, in which an intron was found in the 5' non-coding region and is important for the expression of EF1α gene in leaves (Curie et al, 1991, 1993). The second intron (779 bp) is located in the coding region. Like other plant introns, these two introns in sugarcane EF1α have nearly universally-conserved GT and AG nucleotides at the 5' and 3' ends. They are also strongly enriched in AT nucleotides (FIG. 12) throughout the intron, a feature that is considered to be a requirement of efficient splicing of plant introns (Liu et al. 1996).

In order to map the 5' end of the EF1α gene, a primer extension reaction was done with a 30 bp primer near the translation start site. The transcription start site of EF1α was estimated by gel electrophoresis in parallel with sequencing of the genomic clone containing the translation start codon. There were two different temperatures used for primer extension. When the primer extension was done at 45° C., two bands appeared and no transcription start site (tsp) could be determined. When the reaction temperature was increased to 50° C., only one major band appeared. Based on manual sequencing of the genomic clone, the transcription start site (tsp) is 130 bp upstream of the translation start site.

In order to characterise sequences involved in the regulation of EF1α in sugarcane, about 1,300 bp of 5' flanking DNA was determined by automated sequencing. This promoter shares the common features of other promoters, with its nucleotide composition rich in AT bases. The putative TATA box (TATAAA) is located at 33 bp upstream of deduced transcription start site and a typical CAAT box found in the position 40 bp upstream of TATA box. The base composition plot of the entire EF gene apparently reveals a typical and interesting feature of A and T composition of a plant gene (FIG. 19). There are four AT rich regions: the promoter, two introns as well as 3' untranslated sequences. There is only one small GC rich region, which is in the first exon (untranslated leader sequence).

Other embodiments and uses of the invention will be apparent to those skilled in the art from consideration of the specification and practice of the invention disclosed herein. All references cited herein, including all U.S., and foreign patents and patent applications, are specifically and entirely hereby incorporated herein by reference. It is intended that the specification and examples be considered exemplary only.

Discussion

Gene Expression and Promoter Isolation

The level of gene expression in plants is associated with many factors such as gene copy number, intron, promoter and untranslated leader sequence. Among these factors, promoter strength is especially important when a foreign gone needs to be expressed at very high levels. Finding highly expressed genes and isolation of their promoters from sugarcane may provide tools that are very useful in sugarcane gene transfer studies. Although the widely-used cauliflower mosaic virus 35S promoter is active in dicot plants, it is less active in monocots (Rotfer 1993). To increase gene expression in monocotyledonous plants, a few promoters have been isolated to replace the 35S promoter in transformation of monocot cells (Last et al., 1991; McElroy et al., 1991; Zhang et al, 1991; Christensen et al., 1992). The ubiquitin promoter has been shown to be the best among the recently-available promoters (Christensen et al., 1992; Gallo-Meagher and Irvine, 1993; Schledzewski and Mendel 1994). However, there are few if any reports in plants that have examined how many kinds of mRNAs may be most abundant in any one species, and whether the abundance of these mRNAs is due to promoter strength or gene copy number. Here we used a new approach to rind highly expressed gene promoters in sugarcane. There were four steps in this approach. First, a sugarcane λ phage library was constructed and pooled mRNA was used as a probe to screen the genomic library. Second, the coding region of these genomic clones was identified by a phage DNA Southern hybridisation with pooled first strand cDNA and corresponding cDNA clones were isolated from a sugarcane cDNA library. Third, the copy number of genes was estimated the cDNA clones and genomic clones. GenBank searching and primer extension analysis. This new approach may help to find new promoters useful in sugarcane conferring high levels of expression of transgenes in sugarcane or other taxa.

Genomic Library Construction and Screening

A representative genomic library samples each part of the genome to similar degrees. One of most effective way to do this is by physically shearing of the genomic DNA (e.g. sonication); however this makes the ligation of genomic fragments with vector difficult. An easier way to do this is to partially digest genomic DNA with a frequent cutting restriction enzyme (usually a 4 cutter), which generates ends compatible with one of the multiple cloning sites of lambda vectors. Sau3A1 recognises the 4-base pair sequence GATC, which occurs on average every 256 bp in DNA with a base composition of 50% [G+C] and therefore it is frequently used in λ phage library construction.

The number of clones necessary to provide good coverage of the sugarcane genome can be calculated from the equation of Clarke and Carbon (1996). With an average insert size of 15 kb, the probability of finding any sequence from the sugarcane genome, range from 2,547 to 3,605 Mb for *Sacchrum officinarum* (Arumuganathan and Earle 1991), in a library of $1 \times 10^6$ clones would be greater than 0.99. This is equivalent to a 5 genome-equivalent. In reality, using a restriction enzyme may bias the library and it is therefore worth trying to achieve at least 10× coverage.

We assumed that haploid genome size of sugarcane cultivar we used is approximately 3,000 Mb. The total gene complement of plants is thought to be around 20,000 to 100,000 protein-coding genes. The results from large-scale sequencing of *Arabidopsis* indicated one gene every kb on average (Bevan et al., 1998). If we suggest that the sugarcane has 20,000 to 100.000 protein coding genes, there would be one gene every 30-150 kb on average. That means that every 10 genomic clones have 1-5 different genes if the average insert size of genomic clones is 15 kb. Therefore 100,000 genomic clones may have 10,000 different genes or more. The initial experiment was focused on finding the most highly expressed genes in the sugarcane genome. The logic of screening the genomic library instead of a cDNA library is that we can find the genomic clones containing the highly expressed genes immediately without cDNA library construction. This may be especially useful for isolation of genomic clones by screening with mRNA from different tissues or stages of development without cDNA library construction.

About 100,000 plaques have been screened with first strand cDNA. Twenty-four clones wore selected after comparison of signal intensity among these 100,000 phages. Thirteen clones that continued to display strong signal intensity after second and third screening were further investigated. The 4 genomic clones with the strongest signal were the same gene (SPRP). Northern analysis showed that this gene is actually highly expressed. Southern analysis indicated that the copy number of this gene in sugarcane might be low. Based on these results, the promoter of this gene may be a promising candidate to construct a high-expression-vector cassette for sugarcane transformation.

This work may provide another method to isolate promoters directly from a genomic library for plant transformation purposes. Ubiquitin is a powerful promoter in sugarcane transformation, and we also picked up the ubiquitin gene after genomic library screening. This indicated that direct genomic library screening instead of cDNA selection, may actually be useful in isolating promoters of highly-expressed genes. It may be especially useful to isolate several different tissue-specific promoters at the same time, without cDNA library construction (although we did construct a cDNA library in this work). There are two steps that can be used for tissue-specific promoter isolation. The first phage selection can be used to identify any genomic clones that contained highly-expressed genes in one tissue. The second screening is phage DNA Southern blot or dot blot, which is more sensitive than plaque lifting, to eliminate the highly-expressed genomic clones, which are also expressed in the tissues that are not wanted. The disadvantage of the phage approach is the DNA isolation, which is time consuming, and less DNA yield for each clone compared to plasmid DNA isolation. The long range PCR approach instead of phage DNA isolation may help to isolate tissue-specific promoters more easily and quickly. Hundreds of phages can be picked up in the first screening and selected in the second screening using MMA from different tissues. Sequence database searches may help us to easily predict the promoter region.

cDNA Library Construction

The quality of a cDNA library is an important parameter in cloning a gene and defining its transcriptional unit. Some problems are commonly observed in cDNA library development. First, cDNA clones may be chimeric (Soares 1994). The strategy in the form of a flow chart for cDNA library construction in 1-ZAP is shown in FIG. 20. A high possibility of chimeric clones results from blunt-end ligation of cDNAs during the reaction in which adaptors are ligated to the cDNAs. One of our cDNA clones was found to have an internal poly T tail which suggested a chimeric clone resulting from blunt end ligation of two cDNA clones in the same direction. There is another possibility of formation of chimeric clones during the ligation of the cDNAs to the cloning vector. However, this event is less likely because the cDNAs have two different ends and three cDNA molecules must be joined together before they can be ligated to a vector molecule. In order to minimise the probability of formation of chimeric clones in the above reactions, the adaptor or vector should be present in excess over the cDNAs. Also, it is important to size-select the cDNAs before ligation (Soares 1994). The problem of chimeric clones may be common in many cDNA libraries, although this problem can be minimised. The chimeric clones can be detected by RT-PCR. A pair of primers from both the 5' and 3' ends of the cDNA sequence will not amplify a cDNA fragment if it is chimeric.

The cDNA clone and genomic clone of sugarcane proline-rich protein (SPRP).

There are two major structural proteins known to exist in the plant cell wall, the hydroxyproline-rich glycoprotein and glycine-rich protein (Raines et al., 1991). Sequencing and homology analysis of SPRP1 cDNA clones showed that this gene is highly homologous with wheat WPRP1 (Raines et al, 1991) in both DNA sequence and protein structure. WPPRI was considered a novel cellular protein, which may have a possible role in forming a pan of the cell wall matrix. Northern analysis of WPRPI indicated that this gene is constitutively expressed with a significantly higher level in rapidly dividing or growing tissues. Our data showed the SPRPI gene to be highly expressed in both leaves and stems but only expressed at low levels in the roots. More specific information on the regulation of this gene may be obtained by transformation of sugarcane with the SPRP promoter fused to a reporter gene.

Southern blot analysis of sorghum and sugarcane genomic DNA using SPRPI cDNA as a probe reveals an interesting pattern of bands. One strongly hybridizing band is seen in both *S. propinquum* and *S. bicolor*, suggesting that sorghum may contain only one copy of this gene. Many fainter bands are seen in Southern blots probed with SPRP1, the presence of these fainter bands suggests that there may also be weakly-homologous sequences in sorghum. There is a similar report for the wheat proline-rich protein (Raines et al., 1991). Many minor bands were visualised on Southern blot of wheat genomic DNA when hybridised with the wheat PRP cDNA. The most interesting feature of the SPRP gene is that the Southern analysis indicated a low copy number in sorghum, wheat and sugarcane. The high-level gene expression and low copy nature suggest that the promoter of PRP may serve as a good promoter for sugarcane transformation.

We isolated the genomic subclone that contains the entire promoter and coding region. About 1.7 kb upstream of the translation start site and the region that coded for the 5' end of the cDNA were sequenced. Comparison the nucleotide sequences of the two cDNAs (SPRP1 and SPRP2) to the genomic sequence confirmed that the promoter we isolated here is a promoter of proline-rich protein gene expression. The genomic nucleotide sequence shows 100% identity with the 3' end of untranslated region of the SPRP1 cDNA, but only 97% identity among the coding region. In similar, the nucleotide sequence identity of the 3' end untranslated region between genomic clone and SPRP2 is 96%, which is much higher than sequence identity (83%) of the coding region near the 3' end. There is a similar situation between the two cDNAs (SPRP1 and SPRP2), which reveal a higher nucleotide sequence identity (96%) in 3' end untranslated sequence than coding region (88%). The high level of variation in the SPRP coding region is unknown since most of gene families are more conservative in the coding region. We did not obtain sequence for the entire coding region of the genomic clone because of a highly repetitive sequence in the middle of the gene. We did not find any introns, in all of the genomic DNA regions that were sequenced. More sequencing needs to be done to find out whether this gene has introns, Isolation, Identification and Characterisation of Elongation Factor 1α (EF1α) Gene and its 5' Upstream Sequence In *Arabidopsis thaliana*, the protein EF1α is encoded by a small multigene family of four members (A1, A2, A3, and A4). The A1 promoter has been isolated and its expression pattern has been determined in *Arabidopsis* (Curie et al., 1991). The A1 promoter directed strong transient expression in *Arabidopsis* transfected protoplasts (Axelos et al., 1989; Curie et al., 1991).

In Monocots, a member of the gene family encoding the α subunit translation factor and the corresponding genomic clone has been isolated from maize. There are at least six members of EF1α in maize and its expression is differently regulated in leaves and roots under cold stress (Berberich et al, 1995). Although the complete amino acid sequence has been deduced in maize. The promoter and untranslated leader sequences have not been published. The comparison between our genomic sequence and the maize EF1α genomic sequence indicated that sugarcane and maize have high similarity in the coding region (95%) and less in the intron region (70%). The comparison between our genomic sequence and maize EF1α genomic sequence indicated that the maize genomic clones obtained by Berberich et al. (1995) only contained part of the first intron and 5' untranslated region as well as the entire coding region. We isolated the entire EF1α gene including the promoter region. The structure of EF1α in sugarcane is similar to *Arabidopsis*. Both have two introns with one located in the untranslated region and the other one in the coding region.

The promoter of EF1α in sugarcane shows the common features of plant promoters, with a TATA and CAAT box located upstream of the transcription start site. The promoter and untranslated region including the first intron may be fused to a reporter gene and further transgene expression can be investigated to evaluate EF1α regulation.

REFERENCES

Abencibia A, Molina P R, Riva G de la, Sciman-Housein G (1995) Production of transgenic sugarcane (*Saccharum officinarum* L.) plants by intact cell electroporation. Plant Cell Rep 14: 305-309.

Arencibia A, Vazquez R I, Prieto D, Tellez P, Carmona E R, Coego A, Hernandez L, Riva G A de la, Selman-Housein G (1997) Transgenic sugarcane piano resistant to stem borer attack, Mol Breeding 3: 247-255.

Arencibia A D, Carmona E R, Tellez P, Chan M T, Yu S M, Trujillo L E, Oramas P (1998) An efficient protocol for sugarcane (*Saccharum* spp. L) transformation mediated by *Agrobacterium tumefaciens*, Transgenic Res 7. 213-222.

Arumuganathan K, Earle E D (1991) Nuclear DNA content of some important plant species. Plant Mol Biol Rep 9: 208-219.

Axelos M, Bardet C, Llboz T, Le Van That A, Curle C, Lescure B (1999) The gene family encoding the *Arabidopsis thaliana* translation elongation factor EF-1 alpha., molecular cloning, characterization and expression. Mol Gen Genet. 219: 106-112

Benfey P N, Ren L, Chua N H (1990) Combinatorial and synergistic properties of CaMV 355 enhancer subdomains. F2Y1BO J 91 1685-1696

Berberich T, Sugawara K, Harada M, Kusano T (1995) Molecular cloning, characterization and expression of an elongation factor alpha gene in maize. Plant Mol Biol 29: 611-615

Bevan M, Bancroft I, Bent E, Love K, Goodman H, Dean C, Bergkamp R, Dirkse W I Van Staveren M, Stiekerna W, Drost L, Ridley P, Hudson S A, Patel K, Murphy G. Piffancill P. Wedler H, Wedler E, Warnbutt R, Weltzenegger T, Pohl T M, Terryn N, Gielen J, Villarroel R, Chalwatzis N (1998) Analysis of 1,9 Mb of contiguous sequence from chromosome 4 of *Arabidopsis thaliana*. Nature 391: 485-8

Bevan M W, FlaveU R 13 (1983) A chimeric antibiotic: resistance gene as a seleeable marker for plant cell transformation. Nature 304: 184-187

Bower R, Birch R G (1992) Transgenic sugarcane plants via microprojectile bombardment, Plant 12: 409-416

Bower R, Elliott A R, Potier B A M, Birch R G (1996) High-efficiency microprojectile-mediated cotransformation of sugarcane, using visible or selectable markers, Mol Breeding 2; 239-249

Callis J, Fromm M, Walbot V (1987) Introns increase gene expression in cultured maize cells. Genes Devl 1183-1200

Callis J, Raasch J A, Vierstra R D (1990) Ubiquitin extension proteins of *Arabidopsis thaliana*, Structure, localizadon, and expression of their promoters in transgenic tobacco. J Biol Chern 263A2486-12493

Chen G, Rothnie E M, He X, Hahn T, Futterer j (1996) Elements downstream of the rranscription start site enhance the activity of the rice tungro bacilliform virus (RTBV) promoter in protoplasts derived from cultured rice cells. J Virol 70; 8411-8421

Christensen A H, Quail P H (1996) Ubiquitin promoter-based vectors for high-level expression of selectable and/or screenable marker genes in monocoiyiedonous plants. Transgenic Res 5: 213-218

Christensen A H, Sharrock R A, Quail P H (1992) Maize polyubiquitin genes: structure. thermal perturbation of expression and =script splicing, and promoter activity following transfer to protoplasts by electroporation. Plant Mol Biol 18: 675-689

Curie C, Axelos M, Bardet C, Atanassova R, Chaubet N, Lesture B (1993) Modular organization and development activity of an *Arabidopsis thaliww* EF-1 alpha gene promoter. Mol Gen Cenet Z38. 428-436

Curie C, Liboz T, Bardet C, Gander E, Medale C, Axelos M, Lescure B (1991) Cis and trans-acting elements involved in the acdvation of *Arabidopsis thaliana* A 1 gene encoding the transladon elongation factor EF-1 alpha, Nucleic Acids Res 19: 1305-1310

D'Hont A, Grivet k Feldmann P, Rao S, Berding N, Glasmann J C (1996) Characterization of the double genome structure of modem sugarcane cultivars (*Saccharum* spp.) by molecular cytogenciics, Mol Gen Genct 250. 405-413

Dias MADL (1995) Analysis of water defect stress responsive cDNA clones and the characterization of the genon* clone of gene "I pS" of Lobiolly pine (*Pinus toeda* L), Dissertabon, Texas A & M Elgar G (1997) Preparation of DNA from Hybridization positive phage. In MS. Clark ed., Plant Molecular Biology: a Laboratory manual. Springer-Verlag, Berlin Heidelberg. ppi 13-114

Elornaa P, Helarlutta Y, Griesbach R J, Koffialnen M, Seppanen P, Teeri T H (1995) Transgene inactivation in *Petunia hybrida* is influenced by the properties of the foreign gene. Mol Gon Genet. 248. 649-656

Enriquez-Obregon G A, Vazquez.Padron R I, Pricto-Sumsonov M, De ]a Riva G A, Sciman-Housein G (1998) Herbicide-resistant sugarcane (Saccharum officinarum L) plants by *Agrobacterium*-mediated transformation. Planta 206. 20-27

FAO statistics, 1986 Food and Agriculture Organization, FAO Production Yearbook, Vol. 40, FAO Stadstics Series No. 76, 'Food and Agricultural Organization, Rome FlayeU R13 (1994) Inacdvation of gene expression in plants as a consequence of specific sequence duplication. Proc Nad Acad Sci USA 91; 3490-3496

Fraley R T, Rogers S G, Horsch R B, Sanders P R, Flick J S, Adarns S P, Bittner M L, Brand L A, Fink C L, Fry J S, Galluppi G R, Goldberg 813, HotTmann N L, Woo S C (1983) Expression of bacterial genes in plant cells, Proc Nail Acad Sci USA 80. 4803-4807

Gaille D R, Kado C I (1989) A translational enhancer derived from tobacco mosaic virus is functionally equivalent to a Shine-Dalgamo sequence. Proc Nail Acad Sci USA 86. 129.132

Gaille D R, Sleat D E, Watts J W, Turner P C, Wilson T M (1987) The Y-leader sequence of tobacco mosaic virus RNA enhances the expression of foreign gene transcripts in vitro and in vivo, Nucleic Acids Res IS: 3257-3273

Gallie D R, Walbot V (1992) Identification of the modfs within the tobacco mosaic virus Y-leader responsible for enhancing translation, Nucleic Acids Ros 20: 4631-4638

Gallo-Meagher M, Irvine J E (1993) Effects of tissue type and promoter swength on transient GUS expression in sugarcanc following particle bombardment. Plant Cell Rep 12. 666-670

Gallo-Meagher M, Irvine J E (1996) Herbicide resistant transgenic sugarcane plants containing the bar gene. Crop Sci 36: 1367-1374

Gambley R L, Ford R, Smith G R (1993) Nficroprojectile transformation of sugarcanc meristerns and regeneration of shoots expression beta-glucuronidase. Plant Cell Rep 12; 343-346

Grant S R (1999) Dissecting the Mechanisms of Posttranscriptiorial Gene Silencing, Divide and Conquer. Cell 96:303

Grivet L, D'Hont A, Roques D, Feldmann P, Lanaud C, Glaszmann I C (1996) RFU mapping in cultivated sugarcane (*Saccharym* spp.); genome organization in a highly polyploid and aneuploid interspecific, hybrid. Genetics 142; 987-1000

Hamilton D A, Schwarz Y H, Mascarenhas J P (1998) A monocot pollen-sPecific promoter conWns separable pollen-speciric and quantitative elements, Plant Mol Biol 38:663.669

Herrera-Estrelia L, Block M Y de Messens E, Hernalsteens jip, van Montagu M, ScheU J (1983) Chimeric genes as dorrinant selectable markers in plant cells. EM30 12. 987-995

Holtorf 8, Apel K, Bohlmann H S (1995) Comparison of different constitutive and inducible promoters for the overexpression of transgones in *Arabidopsis thaliana*, Plant Mol Biol 29. 637-646

Honeycutt R J, Sobral B W S, Kelm P, Irvine J E 1992 A rapid DNA extraction method for sugarcane and its relatives, Plant Mol Biol Rep 10. 66-72.

Jobling S A, Gehrice L (1987). Enhanced translation of chimeric messenger RNAs containing a plant viral untranslated leader sequence. Nature 325: 622625

John N Z, Keller G (1995) Characterization of mMA for a prolino-rich protein of cotton fiber. Plant Physiol 108; 669-676

Kay R, Chan A. Daly M and MePherson J (1987) Duplication of CaW 35S Promoter sequences creates a strong enhancer for plant genes. Science 236: 1299-302.

Konez C, de Greys H, Andre D, Deboeck F, van Montagu M, Schell J (1983) The opine synthase genes carried by Ti plasmids contain all signaJs necessary for expression in plants. EMBO J 2. 1597-1603.

Last D I, Brettell R I S, Chamberlain D A, Chaudbury A M, Larkin P J, Marsh E L, Peacock W1 Dennis E S (1991) pEmu: an improved promoter for gene expression in cereal cells. Theor App Genet 81: 581-598.

ILW HX, Filipowtcz W (1996) Mapping of branchpoint nuclcotidcs in mutant pre-mMAs expressed in Plant Cells Plant J 9: 381.389

Luehrsen K R, Walbot V (1994) Addition of A. and U.nich sequence inCreases the Splicing efficiency of a deleted fOrM of a maize intron, Plant Mol Biol 24. 449.463

Luehrsen K R, Walhot V (1991) Intron enhancement of gene expression and the splicing efficiency of introns in maize cells. Mol Gen Genet 225: 81-93

Maas C, Laufs J, Grant S, Korlhage C, Werr W (1991) The combination of a novel stimulatory element in the first exon of the rnaize Shrunken-1 gene with the following intron 1 enhances reporter gene expression up zo 1000-fold. Plant Mol Biol 16.199-207

Maid 1B, Gowda S, Klernan J, Ghosh S K, Shepherd Ri (1997) Promoterlleader deletion analysis and plant expression vectors with the figwort mosaic virus (F" full length transcript (FLT) promoter containing single or double enhancer domains. Transgenic Res 6.143-156.

Matzke A J, Matzkc M A (1998) Position effects and tpigenetic silencing of plant transSenes. Curr Opin Plant Biol L 142-148.

Matzke A I, Matzke M A, Logernann J, Willmitzer L, Schell J (1989) Cisanalysis of the wound-inducible promoter wunl in tmnsgenic tobacco plants and histochernical localization of its expression. Plant Cell 1; 961-968

MLatzke M A, Nutzke A I (1998) Gene silencing in plants: relevance for genome evolution and the acquisition of genomic methylation patterns. Novartis Found Symp 214: 168-180

McElroy D, Blowers A D, Jenes 8, Wu R (1991) Construction of expression vectors based on the rice acdn 1 (Acti) Yregion for use in monocot transformakion. Mol Gen Genet. 231: 150-160

MeElroy D, Zhang W, Cao J, Wu R (1990) Isolation of an efficienc actin Prornoter for use in n*cc transfOrmation, Plant Cell 2:163.71

Meyer P, Saedler H (1996) Homology-dependent gene silencing in plants. Annu Rev Plant Physiol Plant Mol Biol 41: 23-48.

N11tra A, Higgins D W (1994) The *Chlorella* virus adenine methyltransferase gene promoter is a strong promoter in plants. Plant Mol Biol 26: 85-93

Odell J T, Nagy F, Chua N H (198s) Identification of DNA sequences required for acdvity of the cauliflower mosaic virus 35S promoter, Nature 313: 6005

Park Y D, Moscone E A Papp 1, lgiesias V A, Vaucheret H, Matzke AjM (1996) Gene silencing mediated by promoter homology occurs at the level of transcription and results in meiofically heritable alterations on methylation and geneactivity, Plant 19: 193-194.

Raines C A, Lloyd J C, Chao S M, John U P, Murphy G J (1991) A novel proline-rich protein from wheat. Plant Mol Biol 16:663-670

Rathus C, Bower R, Birch R G. (1993) Effects of promoter, intron and enhancer elements on wansient gene expression in sugarcane and carrot protoplasts. Plant Mol Biol 23:613-618

Roach B T (1972) Nobilisation of sugarcane. Proc Int Soc Sugarcanc Tochnol 14:206-216.

Slebertz B, Logemann J, WiRmitzer L, Schell J (1989) cisanalysis of the wound-inducible promoter wun I in transgenic tobacco plants and histochemical localization of its expression. Plant Cell L 961.8.

Sleat D E, Hull R, Turner P C, W1hon T M (1988) Studies on the mechanism of translational enhancement by the Y-leader sequence of tobacco mosaic virus RNA. Eur J Biochern 175.75-86

Srnirnyagina E V, Morow S Y, Rodionova N P, Miroshnichenko N A, Solovey A Gs Fedorkin O N, Atabekov X (1991) Translational efficiency and competitive ability of mRNAs with Y-untranslated alpha beta-leader of potato virus X RNA. Biochide, 73:587-598.

Soares K B (1994) Construction of Directional cDNA librasies. Page 110-114, in book: Automated DNA sequencing and Analysis. Edited by Mark D. Adams Srivastava B L, Cooper M, Mullins R T (1994) Quantitative analysis of the effect of selection history on sugar yield adaptation of sugarcane clones. Theoretical & Applied Genetics 87. 627-640

Tanaka A, Mita S, Ohta S. Kyotuka J, Shimamoto K. Nakarnura K (1990) Enhancement of foreign gene expression by a dicot intron in rice but not in tobacco is correlated with an increased level of mRNA and an efficient splicing of che intron. Nucleic Acids Res 18:6767-6770

Tornashevskiya O L, Solovyey A G, Karpova O V, Fedorkin O N, Rodlonova N P, Morozov S Yu, Atabekov J G (1993) Effects of sequence elements in the potato virus X RNA 5' non-translated alpha beta-loader on its translation enhancing activity. 1 Gen Virol 74: 2717-2724

Topter R, Maas C, Horicke-Grandpierre C, Schell J, Steinbiss H H (1993) Expression vectors for high-level gene expression in dicotyledonous and monocotyledonous plants. Methods Enzymol: 217: 67-78

Voinnet 0, Vain P, AngeU S, Baulcombe D C (1998) Systemic spread of sequence, specific =sgcnc RNA degradation in plants is initiated by localized introduction of ectopic promoterless DNA. Cell 95:177.187

Wang V, Mang W, Cao J, McElroy D, Wu R (1992) Characterization of cis. acting elements regulating transcription from dhe promoter of a constitutively active rice actin gene. Mol *Cell Biol* 12J399-3406

Williams S, Friedrich L, Dincher S, Carozzi N, Kessrnann H, Ward E, Ryals J (1992) Chemical regulation of *Racillus thuringiensis* delta-endmoxin expression in transgenic plants. BiotTech 10: 540-543, W11mink A, van de Yen B C, Dons J3 (1995) Activity of constitutive promoters in various species from the *Liliaceat* Plant Mol Biol 28. 949-955

Zhang W, McElroy D, Wu R (1991) Analysis of doe AcrI Yregion activity in transgenic rice plants. Plant Cell 3:1155-1165

---

The claims defining the invention are as follows:

1. An isolated nucleic acid comprising a nucleic acid sequence, wherein the nucleic acid sequence comprises a promoter, wherein the promoter comprises the sequence of nucleotides 1 to 1967 of SEQ ID NO: 5.

2. The isolated nucleic acid of claim 1 further comprises a nucleic sequence having the sequence of nucleotides 2430 to 3207 of SEQ ID NO:5.

3. The isolated nucleic acid of claim 2 wherein the nucleic sequence of nucleotides 2430 to 3207 of SEQ ID NO:5 is an intron.

4. The isolated nucleic acid of claim 1 wherein the nucleic acid is operable to express an exogenous nucleic acid in a monocot.

5. The isolated nucleic acid of claim 1 further comprising an exogenous nucleic acid under control of the promoter, wherein the isolated nucleic acid is operable to express the exogenous nucleic acid in a monocot.

6. The isolated nucleic acid of claim 5, wherein the exogenous nucleic acid comprises a transgene.

7. The isolated nucleic acid of claim 6, wherein the transgene encodes a gene product selected from the group consisting of bactericidal, insecticidal, and antiviral proteins.

8. The isolated nucleic acid of claim 7, wherein the bactericidal protein is bovine lysozyme.

9. The isolated nucleic acid of claim 7, wherein the insecticidal and antiviral protein is snow drop lectin.

10. An expression vector comprising, in a 5' to 3' direction:
   a promoter having the sequence of nucleotides 1 to 1967 of SEQ ID NO: 5;
   an intron nucleic sequence having the sequence of nucleotides 2430 to 3207 of SEQ ID NO:5;
   an exogenous nucleic acid; and
   a 3' termination sequence.

11. The expression vector of claim 10, wherein the exogenous nucleic acid comprises a transgene.

12. The expression vector of claim 11, wherein the transgene encodes a gene product selected from the group consisting of bactericidal, insecticidal, and antiviral proteins.

13. The expression vector of claim 12, wherein the bactericidal protein is bovine lysozyme.

14. The expression vector of claim 12, wherein the insecticidal and antiviral protein is snow drop lectin.

15. A method expressing of a nucleic acid in a monocot plant comprising:
   providing an expression nucleic acid having a promoter having the sequence of nucleotides 1 to 1967 of SEQ ID NO: 5, an exogenous nucleic acid and a 3' termination sequence; and
   transforming the plant with the expression nucleic acid.

16. The method of claim 15, wherein the expression nucleic acid further comprises an intron nucleic sequence having the sequence of nucleotides 2430 to 3207 of SEQ ID NO:5.

17. The method of claim 15, wherein transforming further comprises biolistically transforming the plant with the expression nucleic acid.

18. The method of claim 15, wherein transforming further comprises *Agrobacterium*-mediated transformation.

19. The method of claim 15, wherein the plant comprises an embryonic callus.

20. The method of claim 19 further comprising regenerating a plant from the embryonic callus.

21. An isolated nucleic acid comprising a nucleic acid sequence, wherein the nucleic acid sequence comprises the sequence of nucleotides 1 to 1967 of SEQ ID NO: 5.

* * * * *

SEQUENCE LISTING

```
<160> NUMBER OF SEQ ID NOS: 5

<210> SEQ ID NO 1
<211> LENGTH: 1172
<212> TYPE: DNA
<213> ORGANISM: Saccharum sp.

<400> SEQUENCE: 1
aagccggaac ctcagcccca gccagaacct ttgccaaaac ctgagcctca gcctaagccc      60
acgcccaaac cagagccaaa gcccaaacca gagccggtgc ccaagcctaa gcctgaacca     120
aaacctgaac cagagcctaa acctcaccct aaaccagaac caaaacctga gcctgagcct     180
gagccaaagc cggaaccaaa accagagcct aagcctgagc ccaagccaga accaaaacct     240
gaaccactgc cgaaaccaga gcctcaacct gagccgaaac cagaaccaaa acctgaacca     300
gtgccgaaac cagagcctaa gcctgagccc aaaccagaac caaaacccga gcctaagcca     360
gaaccaaaac ccgaaccatt gccgaagcct gagcctaagc cagaaccaaa acccgaacca     420
ttgccgaaac cagagcctaa gcctgaaccc aagccggaac caaaacctga accactgccg     480
```

```
aaaccagagc ctaagcctga gcccaagcca gaaccaaaac ccgaaccatt accgaaacca      540
gagcctaagc ctgagcctaa gccagaacca aaacccgaac cactgccgaa gccagagccc      600
aagcctggac caaaacccaa accactgccc aagcctgatc ccaagcctaa ccaaaaccc       660 gaaccactac ccaaaccaga gcctgaaccg aagccaaagc ccaagcctga cccaaaccc       720 aaaccagagc caaagcctga ccaaaaccg gagcctgagc ctgaaccgaa gcccgagcct       780
gagccaaaac cggaacccaa accagagcct aagcctgaac cgaagccaga gcctaagccc      840
gagccaaaac cagaacctaa accaaaacca agccagagc cccaaccaaa accggagcct      900
aagccccaac caaaacctga gcccgaaccc aagcctgagc caaaccaaa gcccgacccg       960 ccgcacatcc caccggcagc tgacaactga tgaagagtcc actagccatt atagcagtat      1020
ctgaataaaa tgccccatga ggccgtagtt gtagcatgca tttgcaggtg ctagcagctg      1080
cttgttgtac ctattctttc tgtgtttgcg tcattttct atgtaatgtt gattacatga      1140
tttttagtgc aaaaaaaaaa aaaaaaaaaa aa                                   1172
```

<210> SEQ ID NO 2
<211> LENGTH: 163
<212> TYPE: PRT
<213> ORGANISM: Saccharum sp.

<400> SEQUENCE: 2

```
Met Ala Ala Pro Arg Arg Leu Ser Ser Cys Cys Leu Leu Phe Ala Val
1               5                   10                  15

Leu Leu Gly Ala Val Leu Ala Thr Ala Thr Ala Phe Phe Glu Gln Ala
            20                  25                  30

Ala Ala Ala Gly Val Gly Leu Gly His Gly Ala Arg Phe Ala Arg Lys
        35                  40                  45

His Gly Arg Ala Ala Ala Glu Leu Pro Gln Pro Glu Pro Gln Pro Lys
    50                  55                  60

Pro Glu Pro Lys Pro Glu Pro Gln Pro Gln Pro Gly Pro Leu Pro Lys
65                  70                  75                  80

Pro Glu Pro Gln Pro Lys Pro Thr Pro Lys Pro Glu Pro Lys Pro Lys
                85                  90                  95

Pro Glu Pro Val Pro Lys Pro Glu Pro Lys Pro Glu Pro Glu Pro Lys
            100                 105                 110

Pro His Pro Lys Pro Glu Pro Lys Pro Glu Pro Glu Pro Lys Pro Glu
        115                 120                 125

Pro Lys Pro Glu Pro Lys Pro Lys Pro Lys Pro Glu Pro Lys Pro Glu
    130                 135                 140

Pro Leu Pro Lys Pro Glu Pro Lys Pro Glu Pro Lys Pro Glu Pro Lys
145                 150                 155                 160

Pro Glu Pro
```

<210> SEQ ID NO 3
<211> LENGTH: 2548
<212> TYPE: DNA
<213> ORGANISM: Saccharum sp.

<400> SEQUENCE: 3

```
actgtccatc atctatcggt tcattcatcc acgatttggc ttgcacaagc catacactgc       60
cgacctagct cgtgtttaga tgcaatttt ttttacaaaa tgctcctgta gcactttttt      120
attgttattt ggaaattagt gtctaatcgt gaactaatta ggcttaaaag attcatctcg      180
```

```
tgaatttcat ctaaactgtg taattagttt tattttttat ctatatttaa tgcttcatgc     240
atgtgtctaa agattcgatg tgatgggaaa tattgaaaat ttttgcaaaa ttttttgcat     300
ctaaactgag ccctacacct cggtcccaga ccgttcgtcg atgaatctgg acaactacct     360
gtccagattt ttattcctat accaacagtt ttttgaatgg agggagtacg aagtcgccag     420
tacgtgtccc ttttaacctg tagtgataaa actgtgaatt tctagataaa cttttgggat     480
gaggccctat ttatctggct tataatccgt cttatttagc ttgttttttc agccggaaca     540 gtattttct ctcacaaaaa atcagccaac agtgttttc agccggctta taaacttttg       600
ggatgcaacc attttgaac cacttttctt tttttaacgt attttctacc acttttcaac      660
cacgcactga cgcacgctat gcatgtaatt caacaagtac tcttattact tactttgtct     720
aattgactgg tttaccatca ccctggacct gcaggcaaag caagatgtgg acactgccgt     780
gtcggtcacg caggaaatca aagttctacg acgacatttg tacggcgcgc ggtacgcatc     840
ttagcgtcct cactctcatc ttctccggcc agcacagccg caatacacgc acacgtac       900 tctcggaacg gtcactacac agtctgatgt gctgcaccgt accggcctgc aatgcaacca     960
tgcatatcat cgatcatgtg tctcacagtg ccgtctgtgt cctttccctt aggcgatcct    1020
gatcttgagc ttcacgagct gagtgcccgc cagccatgca tgcatgatgt ccaccagaca    1080
tgcatgcatg gcacactagc agctcgccat gcataggact agctagctat aggacgatga    1140
tgatctgagc tccatccagg accatgtgca tgcaacagcg cgcgacagat aagatgaca     1200 attgctagcc tggtcatcca tcgtccacac aaaaatatct ttgctacctc aaagcaasgg    1260
aggaaaccta cacagataac aactgactag cctgcagggg atgaatcttc atacatactc    1320
cagtacatag ctcgctcgct ggtcatttgg tcaacagcgg cagcatgcgt cgtcaaacac    1380
aagctaaatg ccttttaccc gtcccgtgta tcatcaaaag ttaacaaacc tacctgtcag    1440
gcagcagcgt atatgtgaaa caagaaatgg atggaagagt ccgtgagaaa gtaaaggtga    1500
aagatacgtg ctactgctat ccgttgaata gcaataaaca cgggcttagc tgttacctac    1560
ccgttgatac ggcggaggcc aaacgtgtaa agcagcttat tttttttaat gagagagtgt    1620
aaagcagcta cttagctggg cagacagccc atccacgcgt ccaaagctgc ttggctctcg    1680
cgcgctataa atccgaccca tggccacacc ccgtcatcca catccacaca cacaacagag    1740
actactcggg cactaccaac agctgctcta gagaaagaga gagagaggca gagagctagc    1800
aacacacagc agagagagaa ctagcaggcg aacttgttgg aggagcagcg gctagccatg    1860
gcggcgccgc gtcgactctc ttcgtgctgc cttctcttcg ccgtgcttct gggagcagtg    1920
ctggccaccg ccaccgcctt cttcgacgaa gcggcggctg ccggcgtcgg gcttggccac    1980
ggcgcccgtt tcgcgcgcaa gcatggacgt gctgccgccg agctgccgca gccggagcca    2040
cagcccaaac ctgaacctaa gccggaacct cagccccagc cagaaccttt gccaaaacct    2100
gagcctcagc ctaagcccac gcccaaacca gagccaaagc ccaaaccaga gccggtgccc    2160
aagcctaagc ctgaaccaaa acctgaacca gagcctaaac ctcaccctaa accagaacca    2220
aaacctgagc ctgagcccaa gccggaacca aaaccagagc ctaagcctga gcccaagcca    2280
gaaccaaaac ctgaaccact gccgaaacca gagcctcaac ctgagccgaa accagaacca    2340
aaacctgaac cagtgccgaa accagagcct aagcctgagc ccaaaccaga accaaaaccc    2400
gagcctaagc cggaaccaaa acccgaacca ttgccgaagc ctgagcctga gcctaagcca    2460
gaaccaaaac ccgaaccatt gccgaaacca gagcctaagc ctgaacctaa gccggaacca    2520
aaacctgaac cactgccgaa accagagc                                      2548
```

<210> SEQ ID NO 4
<211> LENGTH: 1578
<212> TYPE: DNA
<213> ORGANISM: Saccharum sp.

<400> SEQUENCE: 4

| | | | | | | |
|---|---|---|---|---|---|---|
| cacatcaaca | ttgtggtcat | tggccatgtc | gactctggca | agtcgaccac | cactggccac | 60 |
| ctgatctaca | agcttggtgg | tattgacaag | cgtgtgatcg | agaggttcga | gaaagaggct | 120 |
| gcggagatga | acaagcgttc | attcaagtat | gcgtgggtgc | ttgacaagct | caaggctgag | 180 |
| cgtgagagag | gtatcacaat | tgatatcgcc | ctgtggaagt | ttgagaccac | caagtactac | 240 |
| tgtactgtca | ttgatgcccc | tggacaccgt | gacttcatca | agaatatgat | cactcgtact | 300 |
| tcccaggctg | actgtgctgt | tcttatcatt | gactccacca | ctggtggttt | tgaggctggt | 360 |
| atctccaagg | atcgtcagac | ccgtgagcat | gctctccttg | ctttcacact | tggagtgaag | 420 |
| cagatgattt | gctgctgcaa | caagatggac | gccaccacac | ccaagtactc | caaggcccgt | 480 |
| tatgatgaga | ttgtgaagga | agtctcttcc | tacctgaaga | aggttggata | caaccctgac | 540 |
| aagatccact | tgttcccat | ctctggtttc | gaaggtgaca | acatgattga | gaggtccacc | 600 |
| aaccttgact | ggtacaaggg | ccccaccctg | cttgaggctc | tggacttgat | caatgagcca | 660 |
| aagaggcctt | cagacaagcc | cctgcgtctc | ccccttcagg | atgtgtacaa | gattggtggt | 720 |
| attggaactg | ttcctgttgg | gcgtgttgag | actggtgtca | tcaagcccgg | tatggtggtt | 780 |
| accttcggtc | ccagtggcct | tactactgag | gttaagtctg | ttgagatgca | ccatgaggct | 840 |
| ctccaggagg | ctcttcctgg | tgacaacgtt | ggcttcaacg | ttaagaatgt | tgctgtgaag | 900 |
| gatctgaagc | gtgggtatgt | ggcctccaac | tccaaggatg | accctgccaa | ggaggctgct | 960 |
| agcttcacct | cccaggtcat | catcatgaac | caccctgggc | agatcggcaa | cggctacgcc | 1020 |
| ccagtgctgg | actgccacac | ctcacacatt | gctgtcaagt | ttgctgagct | tgttaccaag | 1080 |
| attgataggc | ggtctggcaa | ggagcttgag | aaggagccca | aattcctcaa | gaaccgtgat | 1140 |
| gctggtatgg | tgaagatggt | tcccactaag | cccatggtgg | tggagacctt | ctctgaatat | 1200 |
| cctcctcttg | gtcgctttgc | tgtgcgggac | atgaggcaaa | cggtggctgt | tggagtcatc | 1260 |
| aagagtgtgg | agaagaagga | cccaactgga | gccaaggtga | ccaaggctgc | cgccaagaag | 1320 |
| aaatgaggtg | tctggctggt | tctgtgtttg | cttggggata | cctagtggga | gcttaaaata | 1380 |
| tctcgtcttg | ttcacgttat | tgctgttatt | gcgtgagcaa | ctaaactgtg | ttggcaatgt | 1440 |
| ctgtctggtc | gatttagtac | tgttattttc | gttggttaaa | acaaggttgc | tattgagact | 1500 |
| cgtttctgtt | attttatatc | gaacatcggg | tgtgagccat | gcatggttat | gagttttgtt | 1560 |
| aaaaaaaaaa | aaaaaaaa | | | | | 1578 |

<210> SEQ ID NO 5
<211> LENGTH: 4531
<212> TYPE: DNA
<213> ORGANISM: Saccharum sp.

<400> SEQUENCE: 5

| | | | | | | |
|---|---|---|---|---|---|---|
| atctccgtag | ataactcagg | ctttcaccaa | actttctcgg | tttcaaatta | taagatgttt | 60 |
| aagttttttt | agatacatta | ttttttacta | tgatcaagac | attgtatata | tttaagtgcg | 120 |
| taccaaaagt | cataaatcta | aaaagtcaa | acgtcttata | atttaaaatg | gagggaggac | 180 |
| tttctaactc | ataccacttg | ttcccttgct | ggttattaat | tactacatac | aaagaccaaa | 240 |

```
attgaatagc caaacttgat tctcaaacca actattttat caaaatctat gcttttgtcc    300
atttccaagc aagggaaatt agttgtgaac gtgcaaagta gtaaaggacc cctttccaaa    360
agggagacga gcccacattg ttaggacaaa aaaatcttta gtatattagt tctttattta    420
aagtctatat aattctactc catatatgac attaaagtgt aactggtatc taaagatcta    480
agagcataac aagcataaaa ttcaaactta ttaaatctag gatccccgta cctcccaact    540
cttctgcag tttaattcgc tcacaacgcc tccttctttg atgtttttt ccgctgtacc      600
tgtgccagta taccaaaatt ttaattttt tgagcgacca aaatacctt tcgaatttaa      660
ttttcatgtt tcattttagt tttactacgt ggtatccacc atatactacg tatacaagag    720
caactccaag agatttggta aaattagatg ctaaattgtg agatttagcc attatgtaaa    780
atagaaagtc tatctaaaat gtagaatttt aaaaccagcc taactaaatt ggaaaacaca    840
aatagcaagt aggactcgct agggaaatat ggccagcgag aatggtagga tagccagcta    900
gaaaaaataa aaaccaatat agacagctgt tgtaatgttt ttttaaagaa cattagctgt    960
aaatcgcttt actaatacat tttgctcatg gccacgaggc aggggtcggg tcttgggtct   1020
tttttttttt gaaacttggt aaaacttcat tactcggcta acaaatcgtt agcaacggag   1080
tctatccata taaaaaacaa tagtatgtgt aggtcgaatg ctgttttgt tcatttgtgg    1140
cccatgaagt gtttttttg ggcccaatag cccattcatc catgcctgaa ccctagggcg     1200
tcttccttat aaaaacctag ctccattctg ttctcaaacc ccaacacgca gtcggccgcc   1260
gcagaccggg agtagccgac gcgccgtcac cgtatcctca gatcagcggc gagccgtaac   1320
caagcaactc tgctgacgcc cgacgaggta ctccgccgca cgcgcgcgcg cttctcttcc   1380
ttttcttttc gctgtgcttt gagcctgttt gtttgatgac tagatctact gggtttgtcg   1440
tctatgtgtg atgagacgag ccgattcatg cactggattt ctaatcaagt gttgtttccg   1500
ccgctgctac ctctatttag tgtctatgta tgaatttggt tgcagtttac aactgatttg   1560
tcgagccata aattataacc gtttggtggt tctagactag atccagtttc cgatctatga   1620
tattacgtgg ctgaggcact taactctgtt ttgtgtgtaa gaactgagcc gattcatgtg   1680
ctggagtact aatccaagtt ttcctttcgc ctcgtctaac tctagtatgt actccgtata   1740
taaacttgat tgcagtttgc aactgattct cggccataga ttattactgt tgcgttgttc   1800
attagatcca gtttccgatc tctgatttac ctgcgtaggg tacttcgtct ttggattttc   1860
ctgtccttgt tgattgtttg attactggtt tatttccata tatttatttc taactgtttt   1920
tatctgctat tttgatgtaa gcagcagtgt agcgtttccc ttcagccatg ggtaaggaga   1980
agactcacat caacattgtg gtcattggcc atgtcgactc tggcaagtcg accaccactg   2040
gccacctgat ctacaagctt ggtggtattg acaagcgtgt gatcgagagg ttcgagaaag   2100
aggctgcgga gatgaacaag cgttcattca gtatgcgtg ggtgcttgac aagctcaagg    2160
ccgagcgtga gagaggtatc acaattgata ttgccctgtg gaagtttgag accaccaagt   2220
actactgtac tgtcattgat gcccctggac accgtgactt catcaagaat atgatcactg   2280
gtacttccca ggctgactgt gctgttctta tcattgactt caccactggt ggttttgagg   2340
ctggtatctt caaggatggt cagacccgtg agcatgctct ccttgctttc acacttggag   2400
tgaagcagat gatttgctgc tgcaacaagg tatgattcca ggaattttat gtagtctggt   2460
tcctgatctg atgtgtgatt ccaggaattt tatctagtct ggttcatgat cagaggtgcc   2520
tgtaaatgtg tttcaatagt ctagcaatat ttatgtgcat tcagtgtctc aattatactg   2580
ccttcaagtt actgtatttg cgttctgatt aaatggctta tgtaagctgt atactaaatt   2640
```

```
tgacaaaatg aaacactgat tgcttaaatt gaaaggcatc ttcgtcctat acatgttaat      2700
gtatgatagc aacttgtctt cattagtttg cataatctaa tatgatttt  ccaggacaat      2760 tttcccaatg ggcgatttaa atttatgatt ccacctgatt ttagaaattg tctgaagtag      2820
ttggattgtt ggaatacttg caatgcatat gtagttaaag caaaagggtt tgcataattt      2880
aactgtcttc atatgattgc aattgttact tagtttactt tgtcaattat tataggattt      2940
gatggcatga acctgttaag gtctgtattt tttttgtata cttgctttat atttttacag      3000
cccgcactag ttagtatatg aataaatttg ttaagtaatc tgcctggcgg ttatttctgt      3060
tgaccccaag aaatttcatg ccttaagcaa gtgtagttgg ccagtaattt ttgattatta      3120
tgttgttgca tttttactgt ttgcttgcag tttatgtcac ctatctcatt caactattgg      3180
tattgtttgg gttttgctgt tttacagatg gacgccacca cacccaagta ctccaaggcc      3240
cgttatgatg agattgtgaa ggaagtctct tcctacctga agaaggttgg gtacaaccct      3300
gacaagatcc actttgttcc catctctgga ttcgaaggtg acaacatgat tgagaggtcc      3360
actaaccttg actggtacaa gggcccaacc ctccttgagg ctttggactt gatcaatgag      3420
ccgaagaggc cttcagacaa gcccctgcgg ctcccccttc aggatgtgta caagattggt      3480
attggaactg ttcctgttgg gcgtgttgag actggtgtca tcaagcccgg tatggtggtt      3540
accttcggtc ccagtggcct tactactgag gttaagtctg ttgagatgca ccacgaggct      3600
ctccaggagg ctcttcctgg tgacaacgtt ggcttcaacg ttaagaatgt tgctgtgaag      3660
gatctgaagc gtgggtatgt ggcctccaac tccaaggatg accctgccaa ggaggctagc      3720
ttcacctccc aggtcatcat catgaaccac cctgggcaga tcggcaacgg ctacgcccca      3780
gtgctggact gccacacctc acacattgct gtcaagtttg ctgagcttgt aaccaagatt      3840
gataggcggt ctggcaagga gcttgagaag gagcccaaat tcctcaagaa cggtgatgct      3900
ggtatggtga agatggttcc cacaaagccc atggtggtgg agaccttctc tgaatatcct      3960
cctcttggtc gctttgctgt gcgggacatg aggcaaacgg tggctgtcgg agtcatcaag      4020
agtgtggaga agaaggaccc aactggagcc aaggtgacca aggctgccgc caagaagaaa      4080
tgaggtgtct ggctggttct gtgtttgctt ggggatacct agtgggagct taaaatatct      4140
cgtcttgttc acgttattgc tgttatttgt gagcaactaa actgtgctgg caatgtttgt      4200
ctggttgatt tagtactctt attatcgttg gttaaaacca ggttgctacg ttaagactcg      4260
tttctgttat tttatatcga acatcgggtg tgagccatgc atggttatga gttttgttac      4320 taccttgtt gcagttgtgt gcctgtttac ctgttttgct tgattctaaa cagcatgaat      4380
gattcgctcg ccatacctgt ctgctgcgtt caaatttctg atgattcgct cgtccaaacc      4440
tgtcatgctt gcggttcaaa tttctcatgc actaaaaatc cttttaatct taaaacttgc      4500
caaatcgcat attgaggatt tttgatgaaa a                                    4531
```